US009602917B2

(12) United States Patent
Mulumudi et al.

(10) Patent No.: US 9,602,917 B2
(45) Date of Patent: Mar. 21, 2017

(54) ACOUSTIC COLLECTION SYSTEM FOR HANDHELD ELECTRONIC DEVICES

(71) Applicant: StratoScientific, Inc., Shoreline, WA (US)

(72) Inventors: Suman K. Mulumudi, Snohomish, WA (US); Mahesh S. Mulumudi, Snohomish, WA (US)

(73) Assignee: StratoScientific, Inc., Shoreline, WA (US)

( * ) Notice: Subject to any disclaimer, the term of this patent is extended or adjusted under 35 U.S.C. 154(b) by 90 days.

(21) Appl. No.: 14/617,807

(22) Filed: Feb. 9, 2015

(65) Prior Publication Data

US 2015/0156583 A1    Jun. 4, 2015

Related U.S. Application Data

(63) Continuation-in-part of application No. 14/054,656, filed on Oct. 15, 2013, now Pat. No. 9,414,155.

(51) Int. Cl.
| | |
|---|---|
| *A61B 7/04* | (2006.01) |
| *H04R 1/46* | (2006.01) |
| *H04R 1/28* | (2006.01) |
| *G10K 11/172* | (2006.01) |
| *G10K 11/26* | (2006.01) |
| *H04R 31/00* | (2006.01) |

(52) U.S. Cl.
CPC ............ *H04R 1/46* (2013.01); *G10K 11/172* (2013.01); *G10K 11/26* (2013.01); *H04R 1/2853* (2013.01); *H04R 31/006* (2013.01); *A61B 7/04* (2013.01); *H04R 2499/11* (2013.01)

(58) Field of Classification Search
CPC ...... H04R 1/46; H04R 1/2853; H04R 31/006; H04R 2499/11; G10K 11/172; G10K 11/26
See application file for complete search history.

(56) References Cited

U.S. PATENT DOCUMENTS

| | | |
|---|---|---|
| D214,002 S | 4/1969 | Machlup et al. |
| D269,295 S | 6/1983 | Bloom |
| (Continued) | | |

FOREIGN PATENT DOCUMENTS

| | | |
|---|---|---|
| KR | 10-2011-0047181 | 5/2011 |
| KR | 10-2013-0022141 | 3/2013 |
| (Continued) | | |

OTHER PUBLICATIONS

International Search Report and Written Opinion for PCT/US2014/060493 dated Jan. 15, 2015.
(Continued)

*Primary Examiner* — Regina N Holder
(74) *Attorney, Agent, or Firm* — Foley & Lardner LLP

(57) ABSTRACT

An acoustic collection system for handheld electronic devices is disclosed having a fitted casing with a chestpiece, and a passageway for conducting sound from the chestpiece to a microphone. In one embodiment, the configuration of the passageway can be actively varied by the user to selectively transmit frequencies of interest to the device. In another embodiment, materials with different sound propagation properties may be used to augment or dampen sound within the passage. In another embodiment, a microphone may be placed within the passageway and its position therein varied by the user.

16 Claims, 16 Drawing Sheets

(56) References Cited

U.S. PATENT DOCUMENTS

| | | | |
|---|---|---|---|
| 4,802,550 A | 2/1989 | Poore | |
| 4,893,143 A | 1/1990 | Sheng-Huei | |
| 5,252,787 A | 10/1993 | Moore et al. | |
| 5,357,972 A | 10/1994 | Norlien | |
| D353,196 S | 12/1994 | Savage et al. | |
| D359,958 S | 7/1995 | Frodelius | |
| D394,314 S | 5/1998 | Moore et al. | |
| 6,210,344 B1 | 4/2001 | Perin et al. | |
| D458,369 S | 6/2002 | Helmholz et al. | |
| 6,510,918 B2 | 1/2003 | Bates | |
| 6,757,392 B1 | 6/2004 | Granzotto et al. | |
| 6,790,178 B1 | 9/2004 | Mault et al. | |
| 7,115,102 B2 | 10/2006 | Abbruscato | |
| 7,449,650 B2 | 11/2008 | Richardson et al. | |
| D591,730 S | 5/2009 | Pantaleone | |
| 7,735,598 B2 | 6/2010 | Nakamura | |
| 8,200,277 B2 | 6/2012 | Lee | |
| D669,587 S | 10/2012 | Mayer | |
| 8,287,283 B2 | 10/2012 | Lecat | |
| D676,034 S | 2/2013 | Stuart | |
| D678,379 S | 3/2013 | O'Neill et al. | |
| D678,869 S | 3/2013 | Diebel | |
| D679,699 S | 4/2013 | Piedra et al. | |
| D680,107 S | 4/2013 | Piedra et al. | |
| D685,356 S | 7/2013 | Diebel | |
| D685,363 S | 7/2013 | Murchison et al. | |
| D686,605 S | 7/2013 | Palmeri | |
| D704,183 S | 5/2014 | Guzman | |
| 8,759,675 B2 | 6/2014 | Rajeswaran et al. | |
| D711,956 S | 8/2014 | Adams | |
| 8,863,415 B2 | 10/2014 | Muraco et al. | |
| D717,856 S | 11/2014 | Slawson et al. | |
| D718,291 S | 11/2014 | Hong | |
| D718,760 S | 12/2014 | Davis et al. | |
| 8,939,251 B2 | 1/2015 | Ting | |
| D723,535 S | 3/2015 | Minn et al. | |
| D724,728 S | 3/2015 | Ting | |
| D726,704 S | 4/2015 | Park et al. | |
| 9,042,568 B2 | 5/2015 | Poplaw | |
| D740,267 S | 10/2015 | Diebel | |
| D744,472 S | 12/2015 | Lerenthal | |
| D744,993 S | 12/2015 | Diebel | |
| D746,802 S | 1/2016 | Mulumudi et al. | |
| D746,804 S | 1/2016 | Nousiainen | |
| 9,243,739 B2 | 1/2016 | Peters | |
| D749,554 S | 2/2016 | Park et al. | |
| 2001/0030077 A1 | 10/2001 | Watson | |
| 2004/0109571 A1 | 6/2004 | Yoshimine | |
| 2004/0173401 A1 | 9/2004 | Kurtz | |
| 2004/0220487 A1 | 11/2004 | Vyshedskiy et al. | |
| 2005/0157887 A1 | 7/2005 | Kim | |
| 2008/0146276 A1 | 6/2008 | Lee | |
| 2009/0213264 A1 | 8/2009 | Kim | |
| 2010/0232615 A1 | 9/2010 | Sorlander et al. | |
| 2011/0064236 A1 | 3/2011 | Schubach | |
| 2011/0087135 A1 | 4/2011 | Ferzli et al. | |
| 2011/0170725 A1 | 7/2011 | Liu | |
| 2012/0027237 A1 | 2/2012 | Lin | |
| 2012/0074006 A1 | 3/2012 | Monaco et al. | |
| 2012/0190303 A1 | 7/2012 | Wong | |
| 2012/0320340 A1 | 12/2012 | Coleman, III | |
| 2013/0116584 A1 | 5/2013 | Kapoor | |
| 2013/0170686 A1 | 7/2013 | Lester, Jr. | |
| 2013/0181584 A1 | 7/2013 | Whitten et al. | |
| 2013/0206614 A1 | 8/2013 | O'Neill et al. | |
| 2013/0301863 A1 | 11/2013 | Weaver, III | |
| 2013/0303000 A1 | 11/2013 | Witter et al. | |
| 2014/0005574 A1 | 1/2014 | Ting | |
| 2014/0077044 A1 | 3/2014 | Witter et al. | |
| 2014/0135080 A1 | 5/2014 | Kimball et al. | |
| 2014/0154152 A1 | 6/2014 | Chumanov et al. | |
| 2014/0163422 A1 | 6/2014 | Poplaw | |
| 2014/0243685 A1 | 8/2014 | Patwardhan et al. | |
| 2015/0087926 A1 | 3/2015 | Raz et al. | |
| 2015/0094597 A1 | 4/2015 | Mestha et al. | |

FOREIGN PATENT DOCUMENTS

| | | |
|---|---|---|
| KR | 20130041559 | 4/2013 |
| WO | WO-2011/049293 A1 | 4/2011 |

OTHER PUBLICATIONS

Japanese Office Action Issued Jan. 6, 2015 for Japanese Design Application No. 2014-008230 (no English translation available).

U.S. Office Action Mailed May 15, 2015 for U.S. Appl. No. 29/469,889.

U.S. Office Action Mailed Jun. 2, 2015 for U.S. Appl. No. 14/054,656.

Brazilian Office Action dated Jun. 16, 2015 for Brazilian Patent Application No. BR 30 2014 001702-0 with English translation of portion of document relating to BR 30 2014 001702-0.

Notice of Allowance Mailed Jul. 31, 2015 for U.S. Appl. No. 29/469,889.

U.S. Office Action Mailed Aug. 21, 2015 for U.S. Appl. No. 14/054,656.

Examiner's Report dated Nov. 13, 2015 received for Canadian Industrial Design Application No. 164902.

International Preliminary Report on Patentability dated Apr. 28, 2016, from related PCT application No. PCT/US2014/060493.

US Notice of Allowance dated Apr. 4, 2016, from related U.S. Appl. No. 14/054,656.

International Search Report and Written Opinion dated May 23, 2016, from related PCT application No. PCT/US2016/017038.

US Notice of Allowance dated Jun. 29, 2016, from related U.S. Appl. No. 29/544,019.

Examiner's Report dated Oct. 18, 2014 for Canadian Application No. 156103 (3 pages).

U.S. Appl. No. 61/735,977, filed Dec. 11, 2012, Barry Poplaw.

iPhone Stethoscope Attachment by Jeff Thompson http://www.thingiverse.com/thing:149028 dated Sep. 10, 2013, Retrieved Sep. 25, 2013.

iPhone Stethoscope Attachment Finished as shown in http://www.jeffreythompson.org/blog/2011/12/15/iphone_stethoscope-attachment-finished dated Dec. 15, 2011, Retrieved Sep. 26, 2013.

My Babys Beat http://www.mybabysbeat.com dated Oct. 10, 2013.

Thinklabs Stethoscope App http://www.thinklabsmedical.com/iphone-a-ipod-touch-app.html dated Oct. 10, 2013.

US Notice of Allowance dated Jan. 29, 2016, from related U.S. Appl. No. 29/508,972.

US Office Action dated Feb. 9, 2016, from related U.S. Appl. No. 14/054,656.

US Office Action dated Sep. 8, 2016, from related U.S. Appl. No. 15/203,680.

Extended European Search Report dated Nov. 17, 2016, from related application No. 14853365.6.

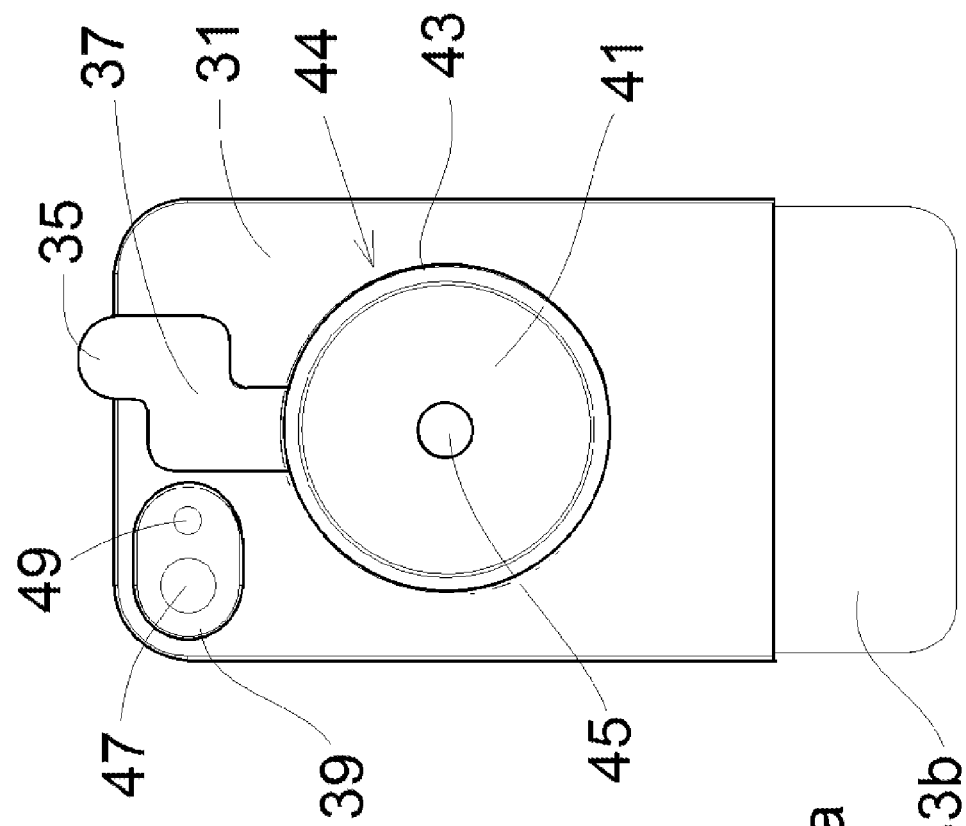
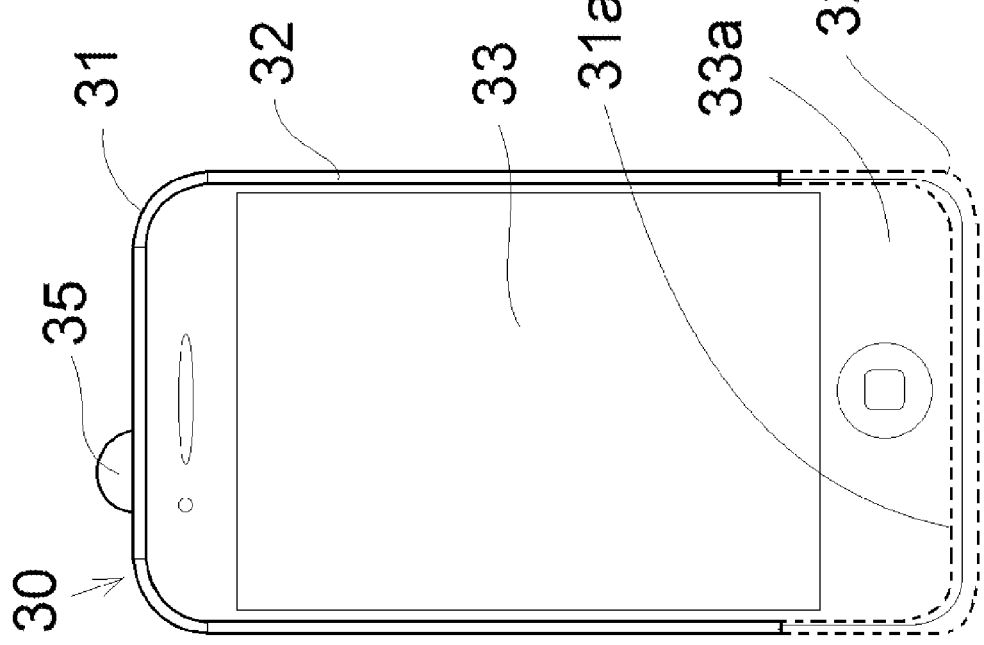

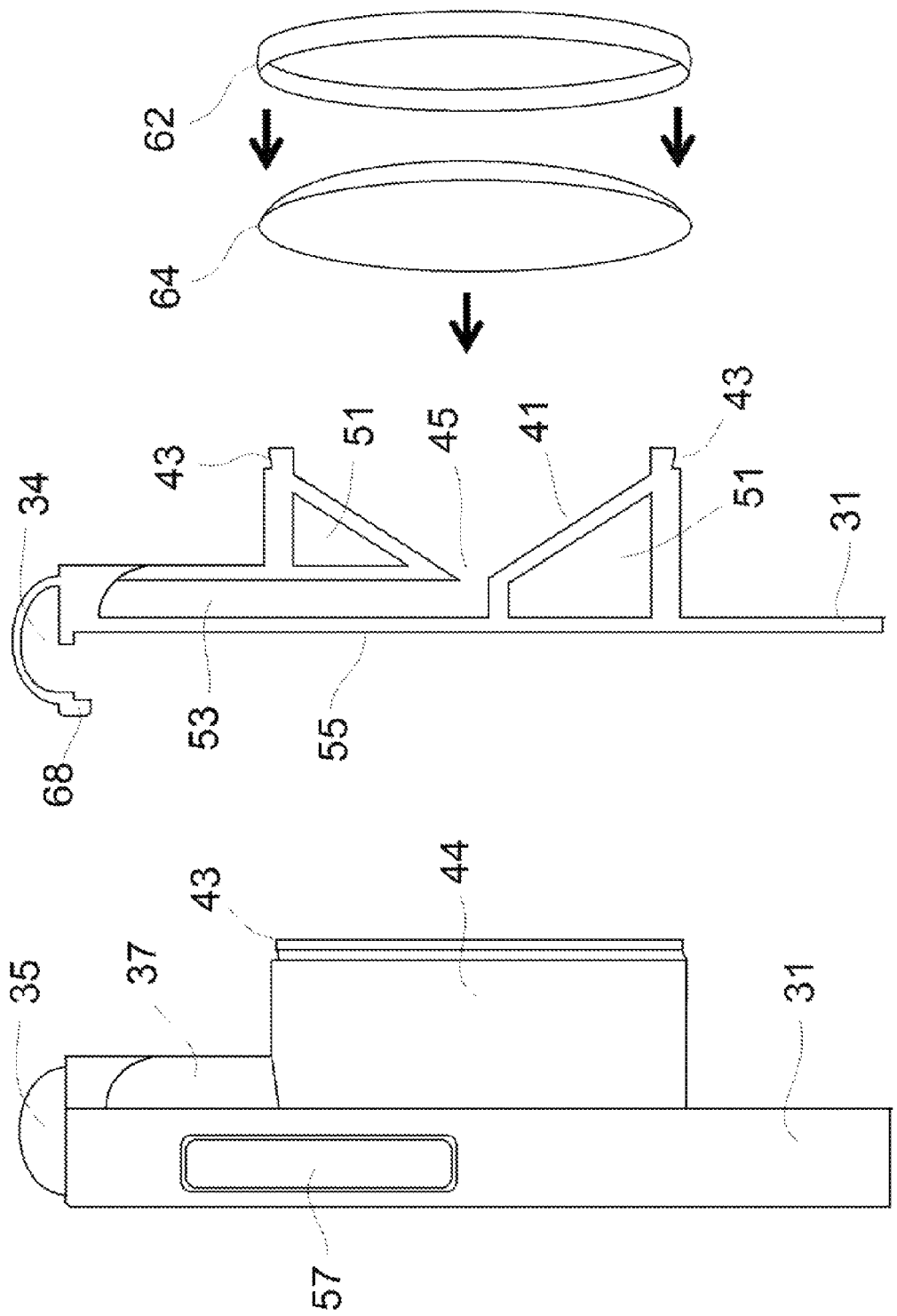

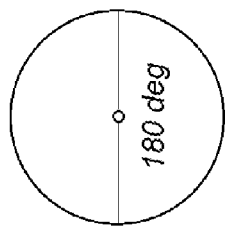
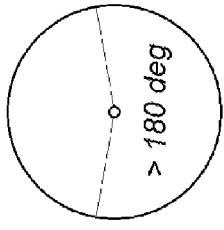
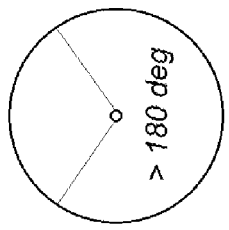
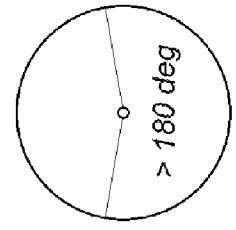
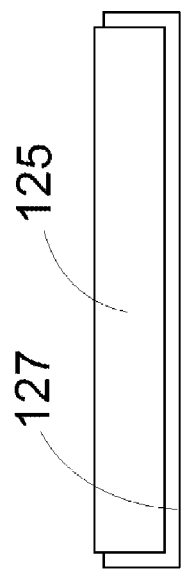
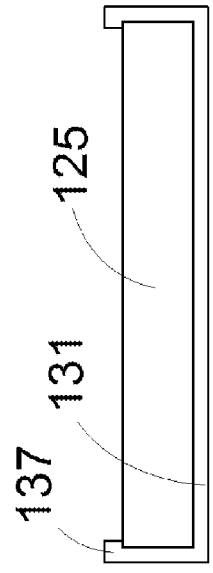
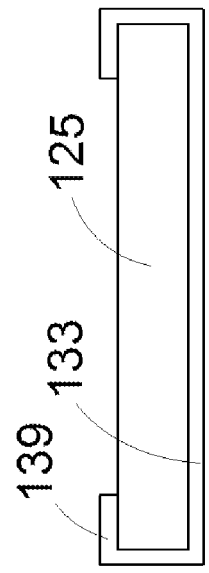
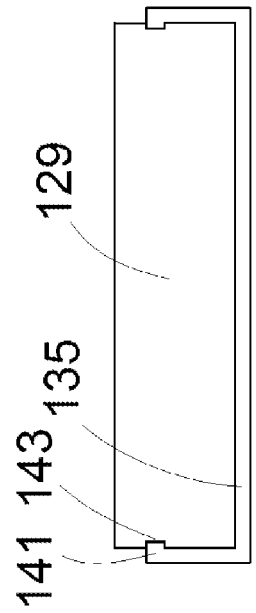
FIG. 2A
FIG. 2B
FIG. 2C
FIG. 2D

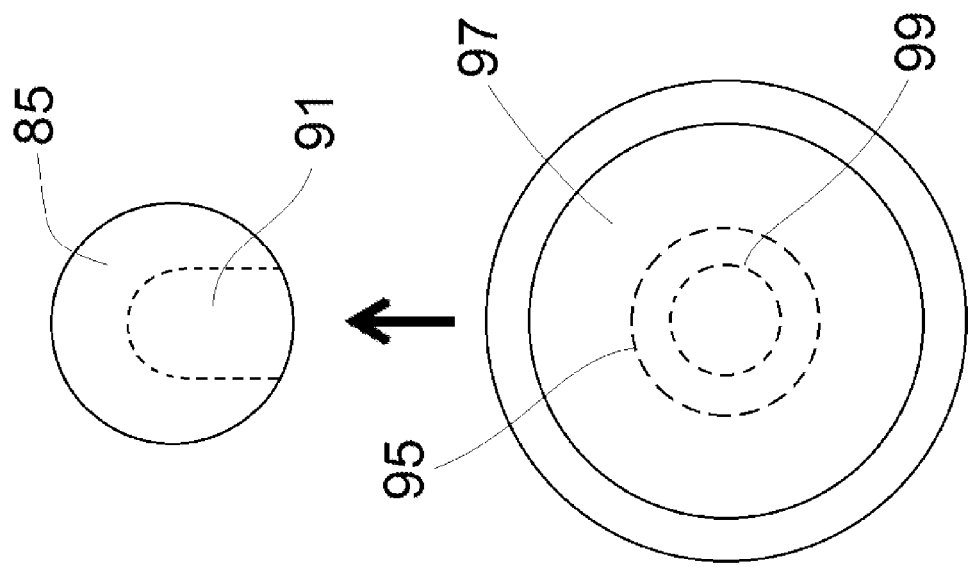
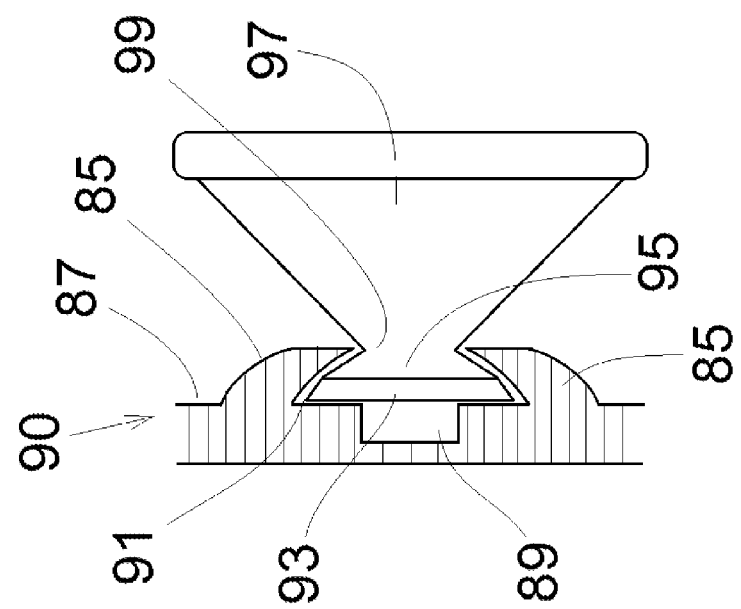

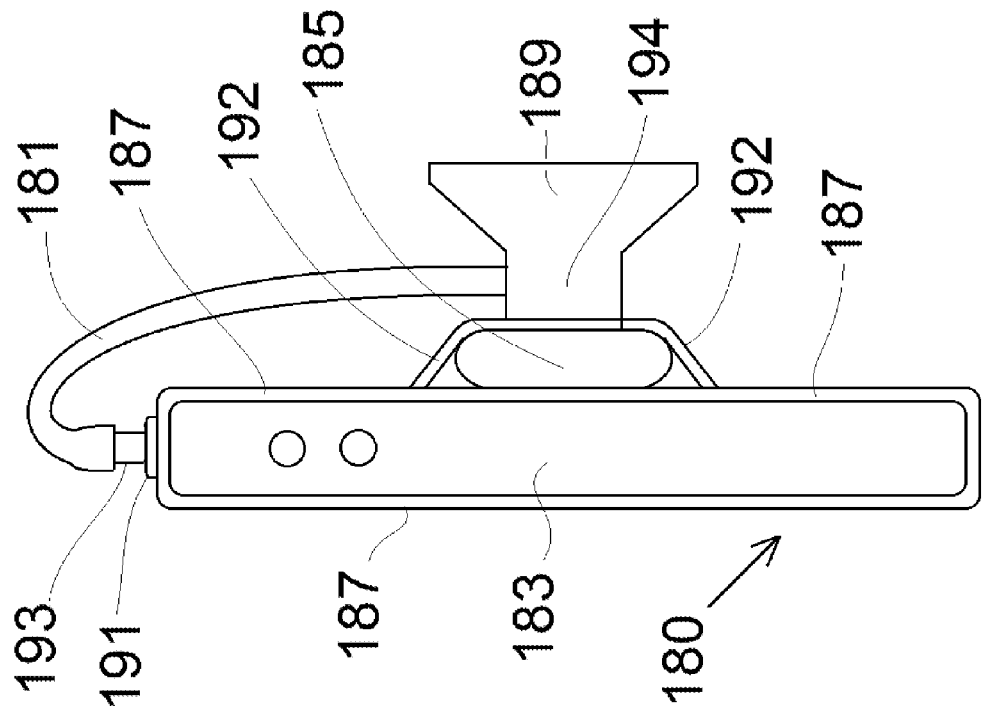
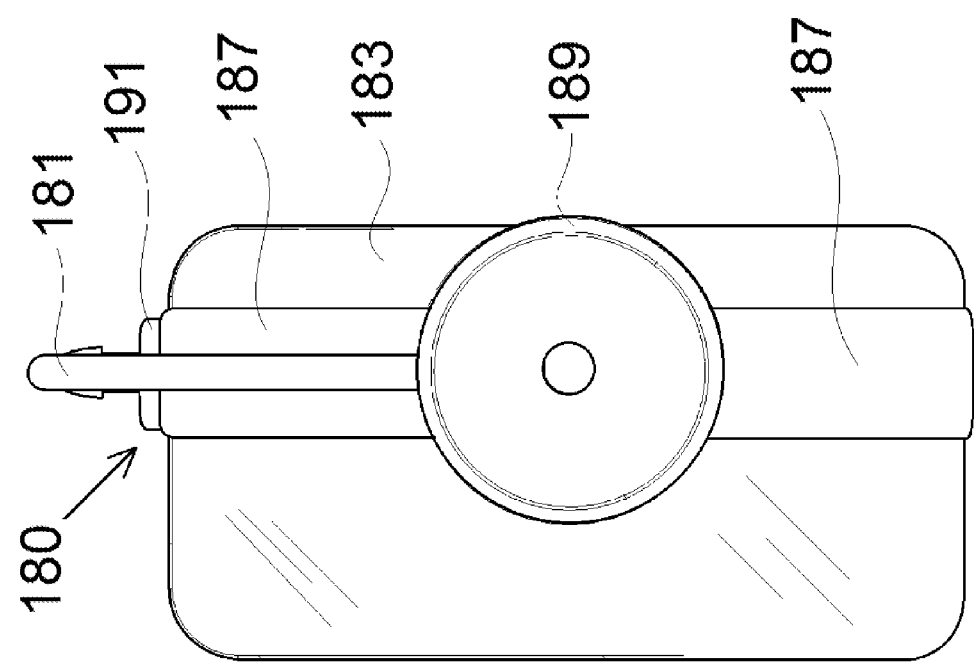

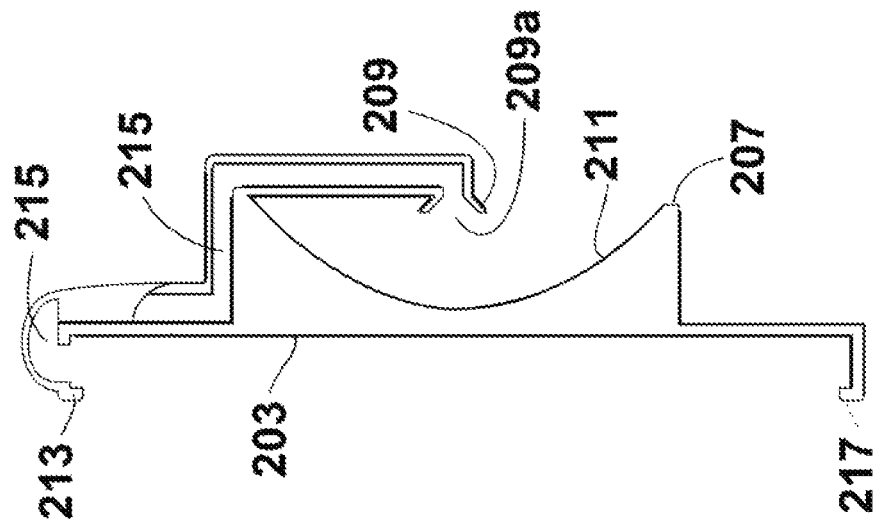
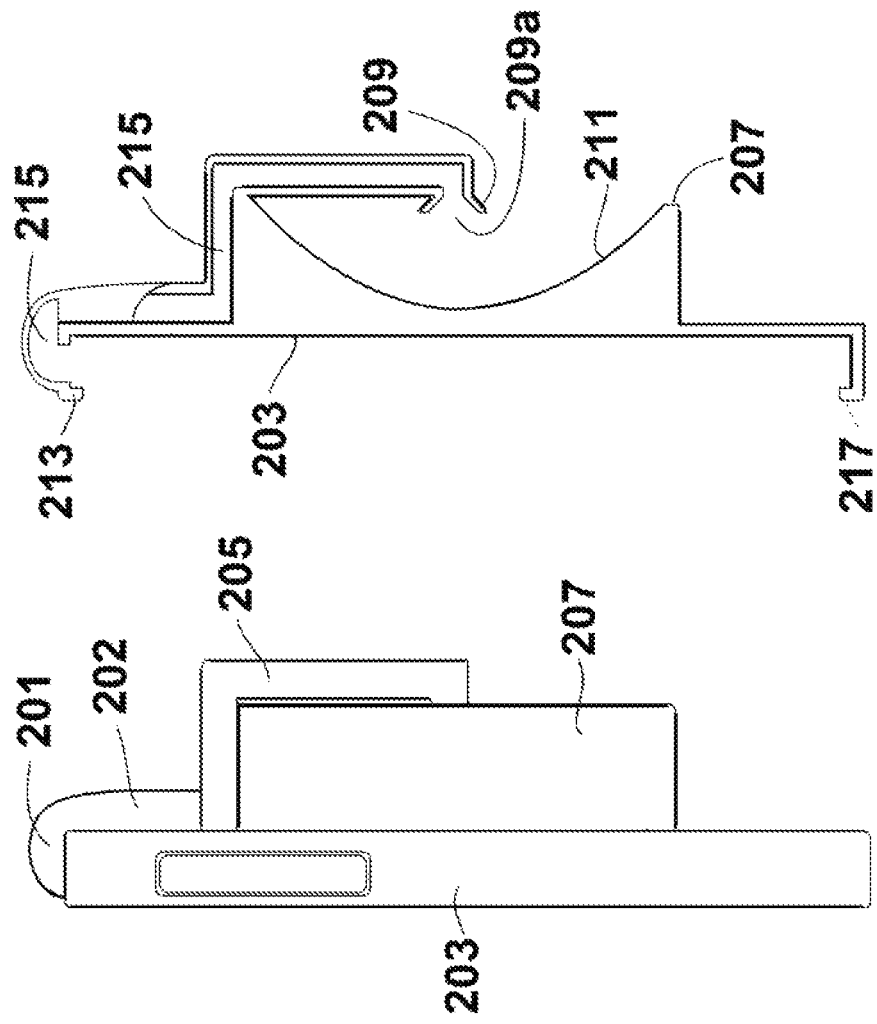
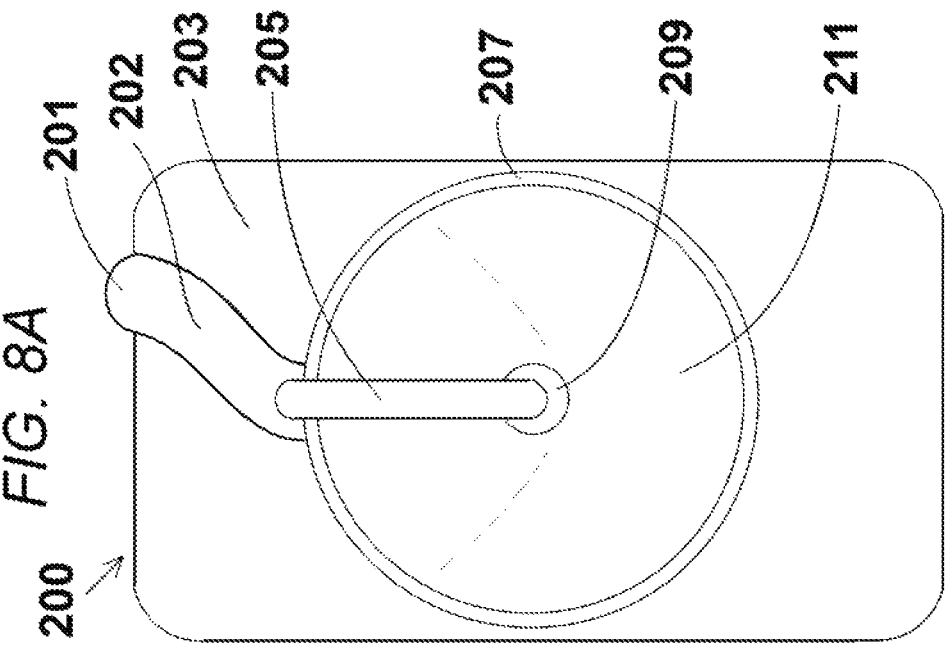

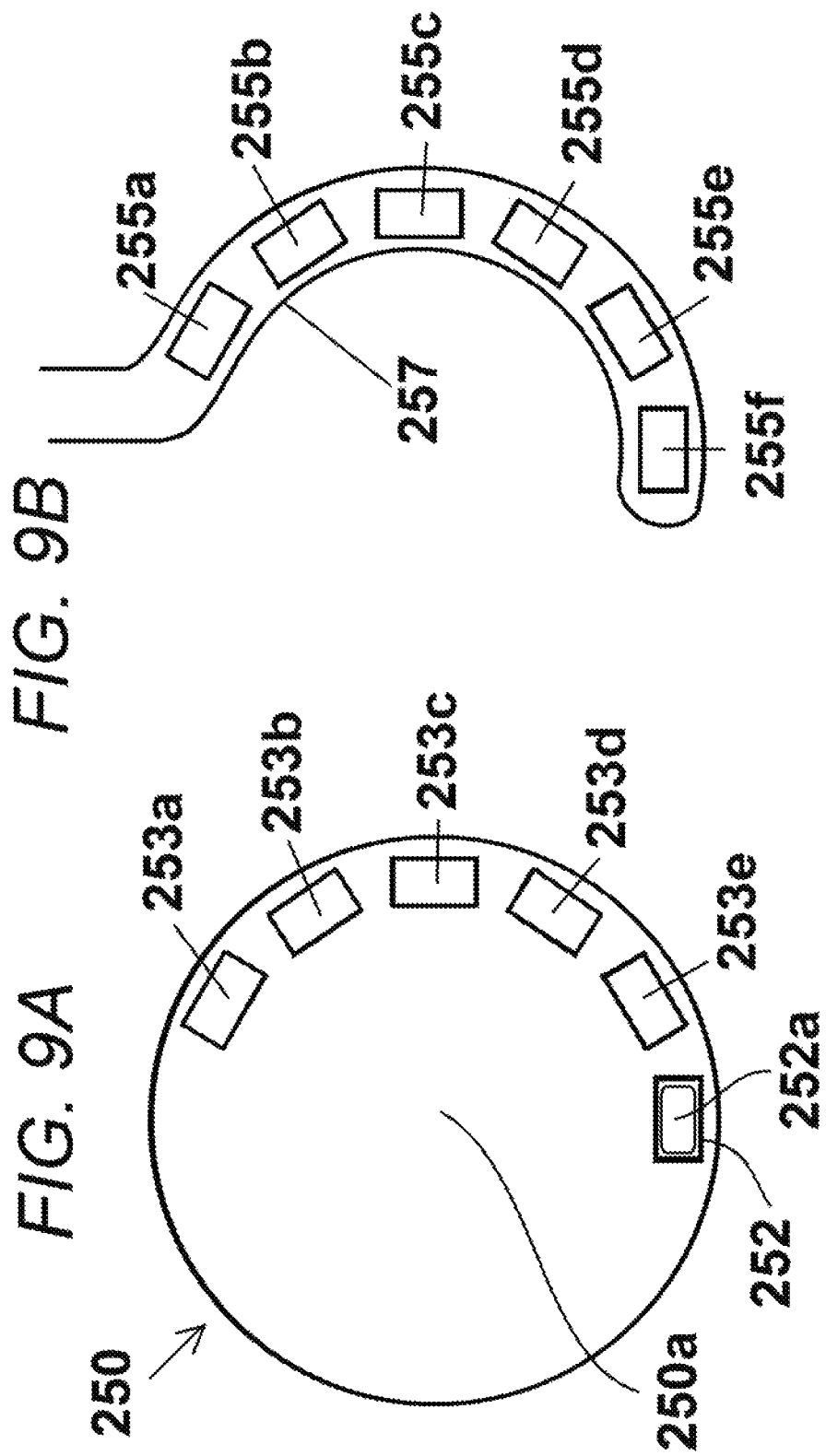

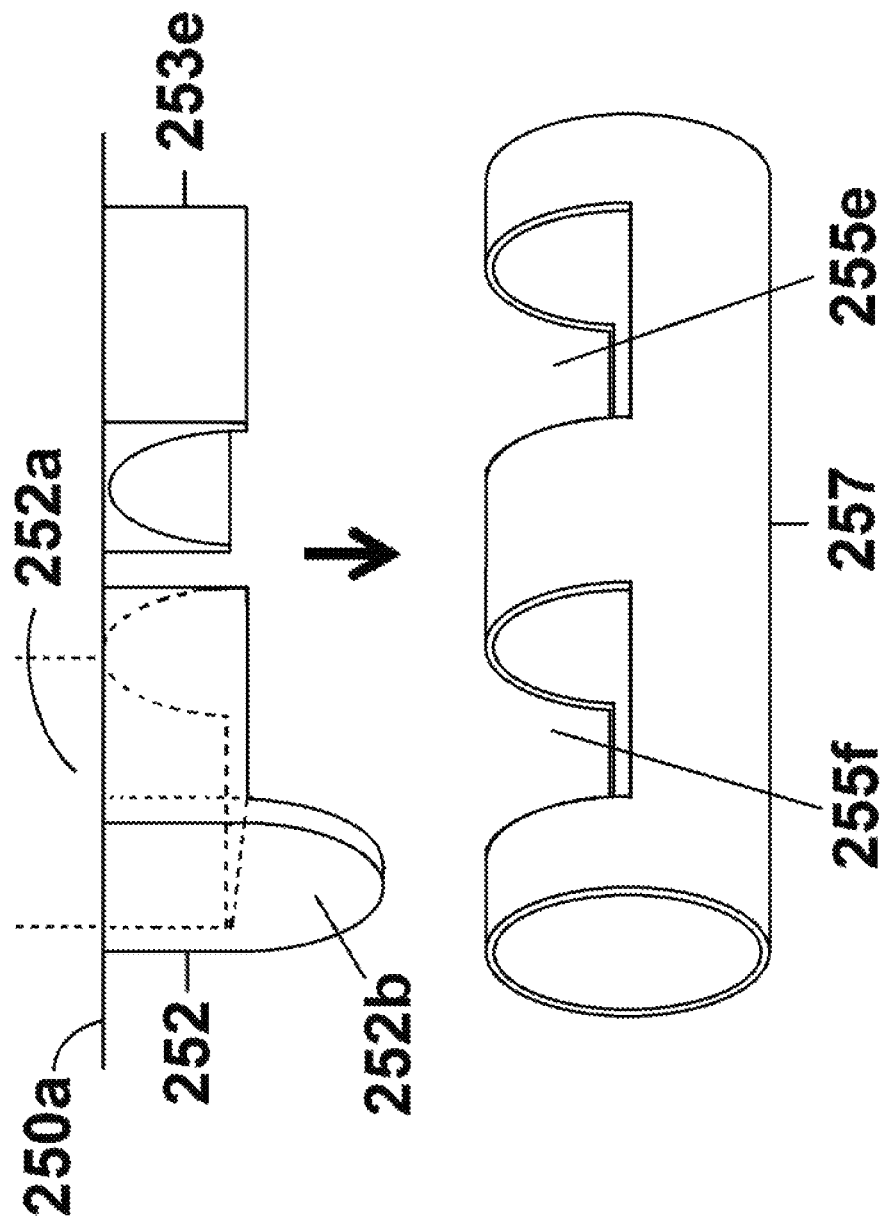

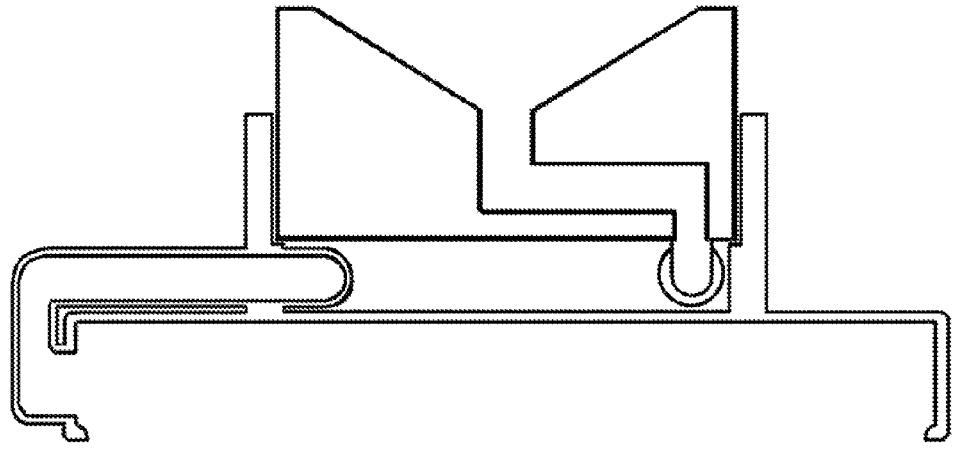
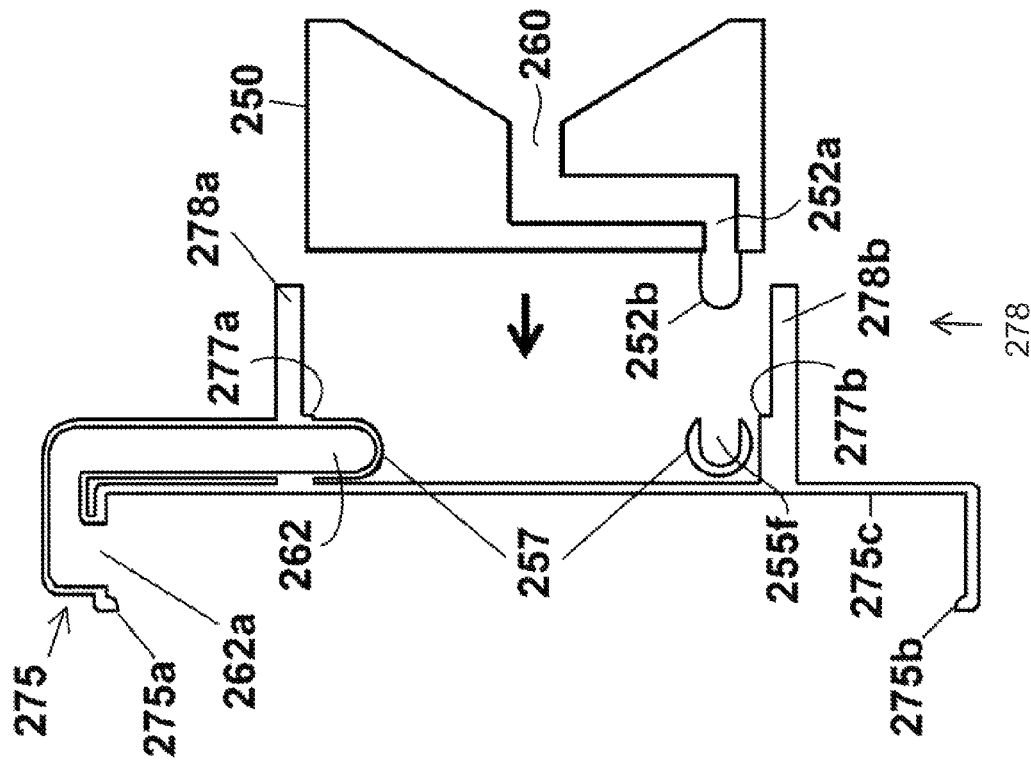

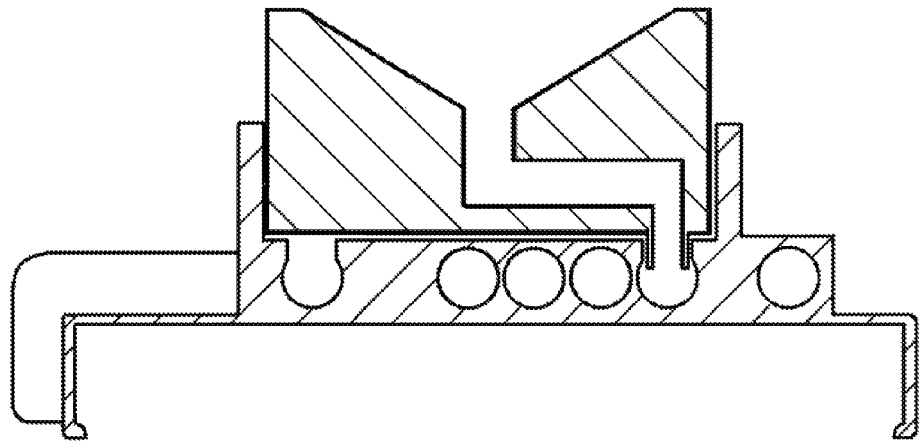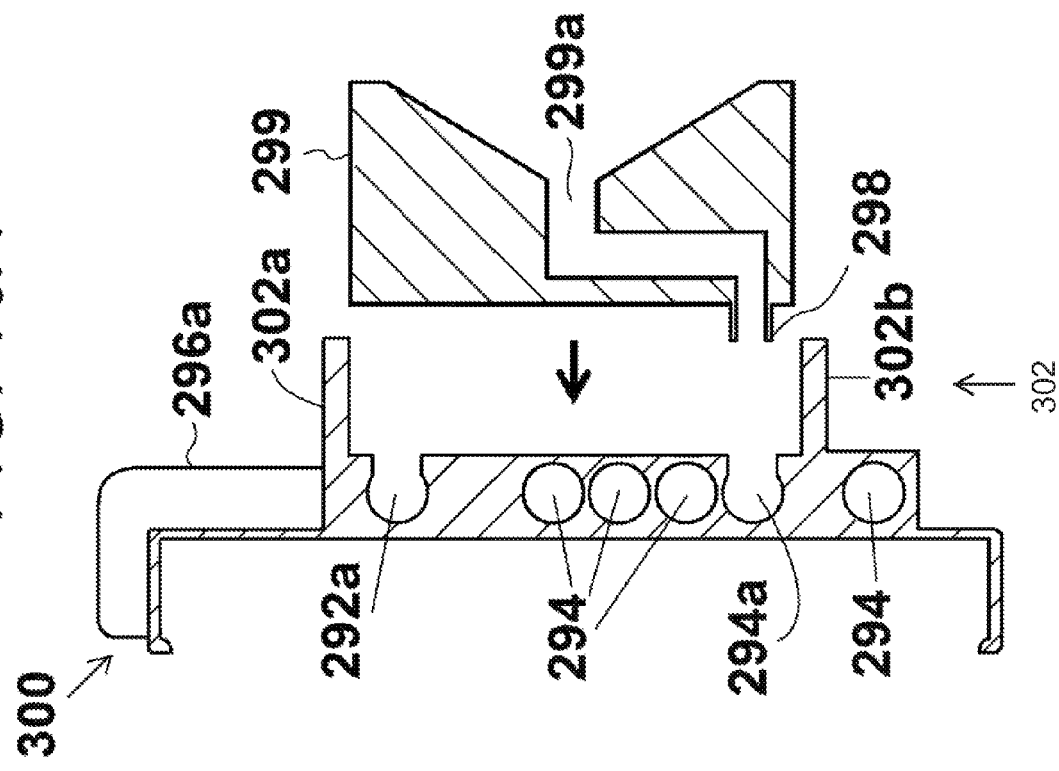

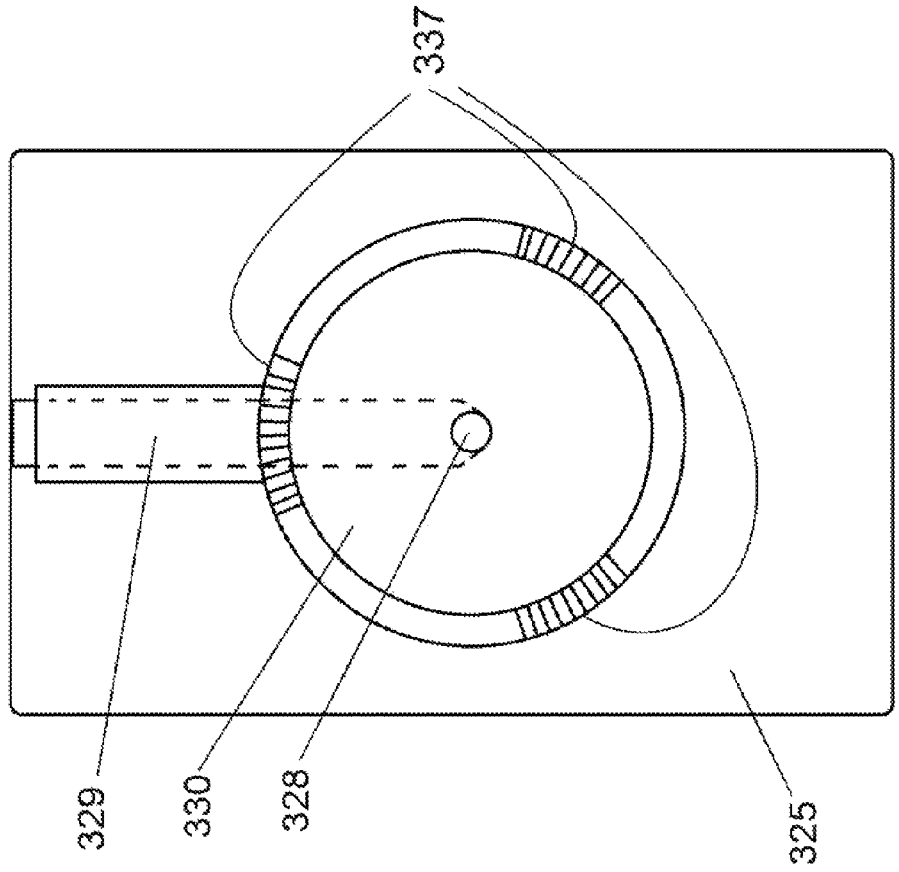
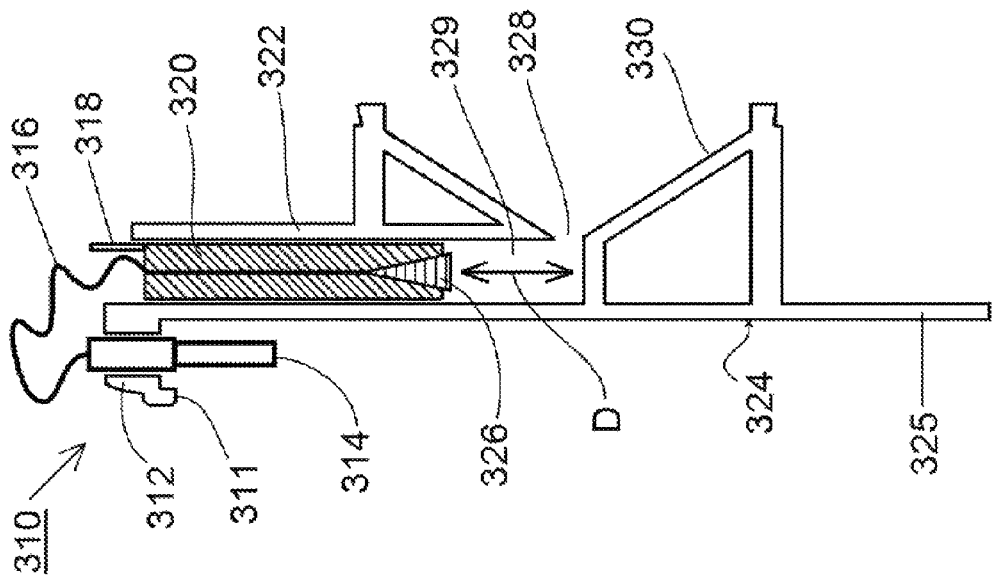
FIG. 11A
FIG. 11B

ACOUSTIC COLLECTION SYSTEM FOR HANDHELD ELECTRONIC DEVICES

CROSS-REFERENCE TO RELATED APPLICATIONS

This application is a continuation-in-part of U.S. application Ser. No. 14/054,656 filed on Oct. 15, 2013, which is fully incorporated herein by reference in its entirety.

FIELD

The present disclosure relates to the field of acoustic augmentation devices, including stethoscopes and long range sound collectors. The present disclosure also relates to the field of attachment accessories for handheld electronic devices such as smartphones and tablets.

BACKGROUND

Acoustic collection devices comprising funnels, elongated tubes and/or listening bells have been used for centuries. As is relevant herein, acoustic collection devices can generally be considered to fall into two categories: (1) stethoscopes for close-range, contact-based sound transmission, and (2) funnels used for contactless, longer range sound detection and amplification, such as parabolic collectors.

The first medical stethoscope is attributed to the nineteenth century French physician René Laennec. Stethoscopes have since come to be used ubiquitously not only by doctors, but also by scientists and craftsmen in a broad range of fields that have a need for basic sound conduction/amplification. The modern stethoscope consists of a chestpiece having a hollow stem connected to a length of hollow tubing that leads to two earbuds.

The chestpiece typically consists of two opposite sides, one having a diaphragm that transmits higher frequency sounds, and the other side having a rigid, cupped bell for transmitting lower frequency sounds. The standard stethoscope includes a semi-rigid frame that serves the dual purpose of mounting the ear buds and allowing the stethoscope to hang around the user's neck.

For longer-range, contactless sound collection, funnels are often used. Though no longer in widespread use, ear trumpets were traditionally used to assist people with hearing nearby conversation or sounds. Modernly, parabolic microphones have come into ubiquitous use for gathering sound waves traveling over distances as great as several hundred yards. The design of a parabolic microphone is fairly straightforward: a cone with a parabolic inner wall focuses incoming sound waves at the geometric focal point of the parabola. A microphone is mounted at the focal point to collect the sound. Alternatively, a tube with an opening may be placed at the focal point, and the sound conducted through the tube to a listening location.

In the present disclosure, the generic term "acoustic collector" or "collector" will be used to refer to acoustic collectors in the nature of both (1) stethoscope chestpieces and (2) longer-range, contactless sound collectors, such as funnels and parabolic collectors. These longer-range, contactless acoustic collectors may also be referred to as "open air" collectors because they are not pressed against a surface in the manner of a stethoscope chestpiece. Where the term "stethoscope chestpiece" or "chestpiece" is employed, it should be noted that although this disclosure will use those terms to refer to a unit containing a diaphragm and/or a bell, such a unit need not only be used in conjunction with medical evaluations. The "chestpiece" might also be used for any number of applications that benefit from being able to detect sound vibrations through a material. The size and shape of the chestpiece might also vary, along with the type and sensitivity of the diaphragm and/or bell. As used herein, "chestpiece" refers broadly to any unit having a surface for resting against a sound-transmitting material, and a hollow interior for transmitting that sound out through a stem.

With the advent of handheld electronic devices, some have proposed alternative designs for stethoscopes that call for incorporating them with electronic sound recorders and wireless transmitters. For example, it has been proposed to attach a stethoscope chestpiece to an electronic recording device mounted along the tube running to the stethoscope's earbuds. This "in-line" device may be equipped with a microphone and Bluetooth-type transmitter for wirelessly delivering a sound recording.

It has also been proposed that a small stethoscope diaphragm be built into the back of a cellular phone. This design is of limited use, however, because, it would require manufacturing a cellular telephone with a small diaphragm already "embedded" into main body of the phone. This is a specialty-purpose application that most cellular phone manufacturers would not consider. Furthermore, embedding a small diaphragm within the phone limits its size.

Another proposed solution is to physically connect a tube from the chestpiece to the microphone of a cellular phone. Such a design proposes that a phone have a microphone at one end, and that an adapter connects the stethoscope tube directly to the end of the phone equipped with the microphone. These proposals call for the chestpiece to be physically separate from the main body of the electronic device, and in some cases connected only by a long length of tubing. The disadvantages of such proposals include at least: (1) instability of the mounting, (2) difficulty of handling the portable electronic device and the chestpiece as separate items, and (3) poor sound quality and conduction.

OBJECTS OF EMBODIMENTS OF THE INVENTION

In light of the foregoing disadvantages of the prior art, it is an object of embodiments of the present invention to provide an acoustic collector mounting system that allows a stethoscope chestpiece or open air collector to be mounted directly to a handheld electronic device as part of a fitted casing.

It is a further object of embodiments of the invention to allow the mounting of an acoustic collector to modern handheld electronic devices such as smartphones and tablets.

It is a further object of embodiments of the invention to allow for the removable mounting of an acoustic collector directly on a handheld electronic device case.

It is a further object of embodiments of the invention to conveniently allow a variety of stethoscope chestpieces to be mounted to a variety of different handheld electronic devices using a universal attachment mechanism.

It is a further object of embodiments of the invention to allow persons to use a handheld electronic device such as a smartphone to amplify sounds across a room, or a longer distance.

It is a further object of embodiments the invention to provide a means for allowing a user to selectively enhance certain sound frequencies or limit reception to certain sound frequencies.

SUMMARY

The foregoing objectives are achieved by supplying a fitted casing that wraps around at least part of a handheld electronic device. The casing is designed to allow affixing of the acoustic collector to the handheld electronic device, and may include an embedded tube running from one or more of the device's microphones to the collector. The acoustic collector may be a stethoscope chestpiece or a longer-range open air collector, such as a parabolic collector. In certain embodiments, the casing may take the form of a band whose length can be adjusted to fit a variety of electronic devices. In preferred embodiments, the portable electronic device is equipped with software that allows the user to selectively amplify and/or limit certain sound frequencies.

In other embodiments, the length of the air passage between the collector and the sound collection point may be designed to have a particular length or configuration to make it better able to collect sounds in a particular range of wavelengths. The device can be further modified to permit the air passage to be adjustable, such that the user can change its shape and/or length to suit a particular sound collection need.

In yet other embodiments, the device may be designed with certain features to accommodate dual use of the device as a sound collector and as a recording device or telephone while the fitted casing is attached to the device. For instance, the channel within the casing that conducts sound to the electronic device's microphone may have an openable portal to allow the user to speak into the microphone while the casing is on the device.

In further embodiments, a microphone may be embedded within the air passage of the device, and be configured to transmit sound recordings to the electronic device either wirelessly or via a direct wired connection.

BRIEF DESCRIPTION OF THE DRAWINGS

FIG. 1A is a plan view of an embodiment of the invention.

FIG. 1B is a plan view of the opposite side of the embodiment shown in FIG. 1A.

FIG. 1C is a side external view of the embodiment shown in FIG. 1A.

FIG. 1D is a side cross-sectional view of the embodiment shown in FIG. 1A, also showing other attachable components.

FIGS. 2A, 2B, 2C, and 2D are cross-sectional schematic views of casings attached to various devices. The circular diagrams on the right of each of these figures are abstract representations of the extent to which the casings encircle the devices.

FIG. 4A is a side view of a portion of an embodiment of the present invention, including a partial cross-sectional view indicated by stripes.

FIG. 4B is a plan view of the portion of the embodiment shown in FIG. 4A.

FIG. 7A is a plan view of another embodiment of the present invention.

FIG. 7B is a side view of the embodiment shown in FIG. 7A.

FIG. 8A is a plan view of another embodiment of the present invention.

FIG. 8B is a side view of the embodiment shown in FIG. 8A.

FIG. 8C is a side cross-sectional view of the embodiment shown in FIG. 8A.

FIG. 9A is a plan view of a component of an embodiment of the present invention.

FIG. 9B is a plan view of another component of an embodiment of the present invention.

FIG. 9C is a perspective and partial cross-sectional view of portions of two components of an embodiment of the present invention.

FIGS. 9D and 9E are side cross-sectional views of an embodiment of the present invention.

FIGS. 10A and 10B are side cross-sectional views of an embodiment of the present invention.

FIG. 11A is a side cross-sectional view of an embodiment of the present invention.

FIG. 11B is a front plan view of the embodiment of the invention depicted in FIG. 11A.

DETAILED DESCRIPTION

Figure 3:
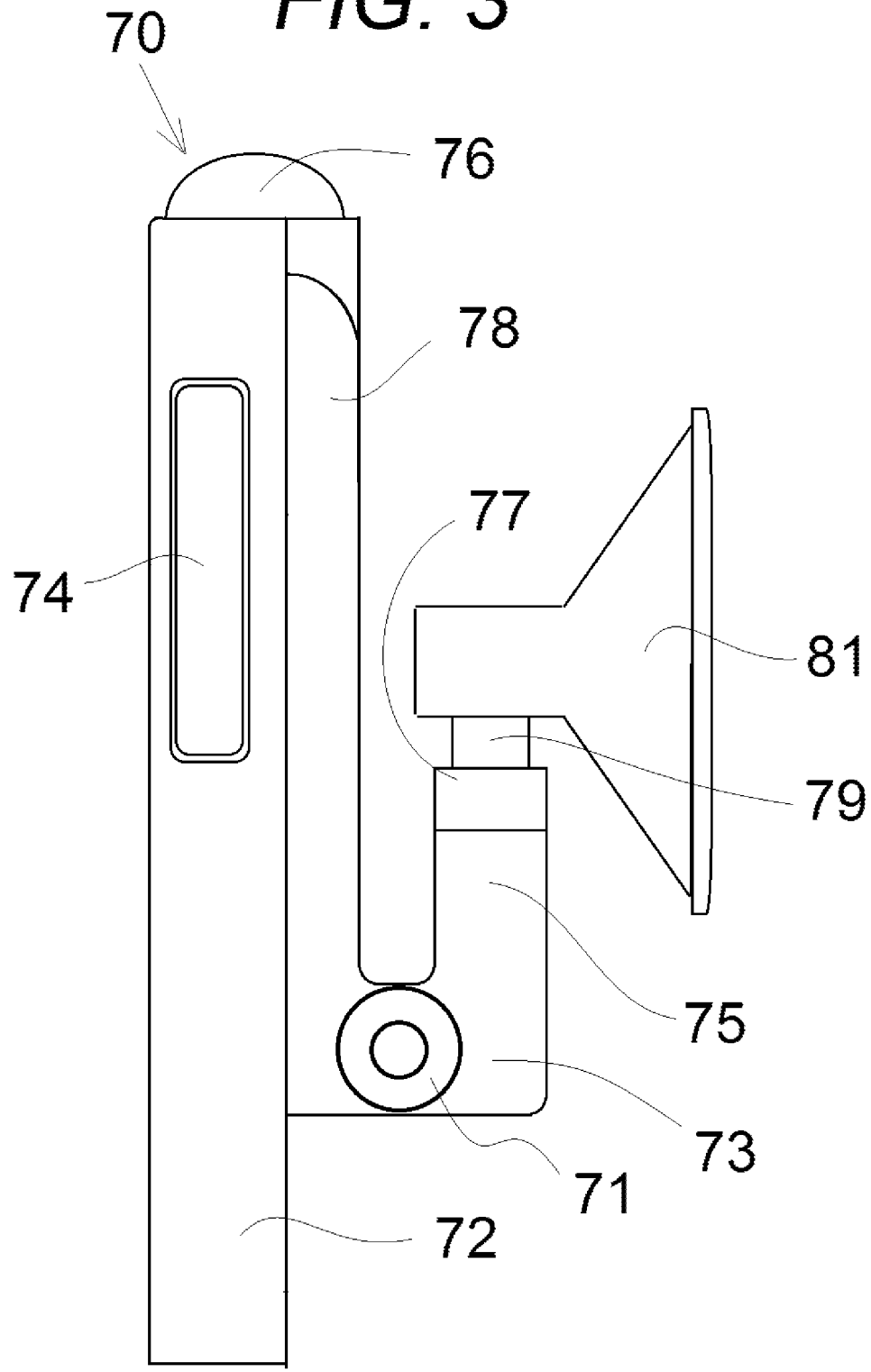
FIG. 3 is a side external view of another embodiment of the present invention.

FIG. 1A depicts an embodiment 30 of the present invention. A sleeve/casing 31 is fit snuggly around a handheld electronic device 33 having front face 33a. The casing 31 is provided with a lip 32 that clasps the edges of device 33, slightly overlapping the front face 33a. The casing 31 may be made of any number of materials, including polymeric material having sufficient rigidity such that it will keep lip 32 clasped about the edges of the device 33 during normal use.

As shown, casing 31 only covers the upper portion of device 33. In this mode, casing 31 should have sufficient elastic tension to exert a squeezing force on device 33 to help keep lip 32 engaged and prevent casing 31 from slipping off device 33. In most circumstances, the overlap of lip 32 on the front face 33a need only be barely visible to achieve the desired clasping effect, so long as the casing is sufficiently rigid to keep the rim in place. Adding a rubberized layer or texturing to the surface of casing 31 contacting the device 33 will also improve the casing's grip.

Alternatively, casing 31 can be designed to wrap more completely around the device as shown by dotted lines representing lower casing portion 31a. Casing portion 31a continues lip 32 as lip 32a, which also clasps the sides of the device 33 and slightly overlaps the front face 33a. When the casing 31 is designed in this manner, it is less likely that device 33 will slip out, and consequently the casing may be made of a more flexible or rubbery material, having sufficient elastic tension that it will keep lips 32 and 32a in overlapping engagement with front face 33a.

The overlapping aspect of the rims just discussed can also be described as the rim "hooking onto" at least a portion of the device such that the casing material wraps around at least a portion of the device by more than 180 degrees, even if the overlap is only slight. This concept is depicted visually in FIGS. 2A, 2B, 2C, and 2D. FIG. 2A is a cross-sectional view of a device 125 partially wrapped with a casing 127. The casing 127 does not hook onto the device, and instead only covers three sides that are at right angles to each other. The arc covered by casing 127 is therefore only 180 degrees, which can be understood by thinking of the device 125 in the abstract as the circle shown in the diagram to the right of the figure.

Referring to FIG. 2B, device 125 is encased by casing 131 which has a lip 137 slightly overlapping the front face of the device. In this instance, the arc covered by the casing 131 is slightly greater than 180 degrees. Similarly, in FIG. 2C, the arc covered by casing 133 about device 125 is greater than 180 degree by virtue of lip 139. If the casing completely encircled the device, we would say it covered an arc of 360 degrees.

FIG. 2D depicts an alternative arrangement in which device 129 has an indentation 143 that allows lip 141 of casing 135 to "hook onto" the device 129. The arc covered by casing 135 is therefore slightly greater than 180 degrees.

Generally speaking, "hooking onto" a device will require that the casing at least partially cover three faces of the device, and that two opposing edges of the casing have lips that each overlap a fourth surface of the device.

Casings of the kind just described are already made by manufacturers of smartphone accessories, such as Incase Designs Corporation, and their construction is known in the art. To the applicant's knowledge, however, no handheld electronic device casing manufacturer has yet proposed incorporating a stethoscope chestpiece with such a casing.

Returning now to FIG. 1A, the microphone end 35 of hollow tube 37 (shown in FIG. 1B) is visible at the top of device 33. The location of the microphone end 35 is dictated by the location of the recording microphone on the device. In many modern smartphones and tablets, there may be more than one microphone on the device. In the case of the iPhone 4S, for example, there are two microphones present. A first microphone has an aperture located off-center on the top of the device. A second microphone (which is used for picking up voice during normal telephone operation) is located off-center at the bottom of the device. Either microphone could be used for the invention, but the top microphone is preferred because it enables the user to audibly interact with the device (i.e. phone call, digital voice assistant, voice recording, etc.) without removing the casing from the device.

Referring now to FIG. 1B, the other side of embodiment 30 is depicted. An opening 39 in casing 31 exposes the camera aperture 47 and flash element 49 of device 33, shown here with its rear face 33b partially exposed. It may be advantageous to combine audio recordings made with the acoustic collector with visual recordings (still images or video) made by the camera. For example, if the invention is used as a medical stethoscope, the audio recordings may be combined in the same computer file with pictures or video of the patient taken which the audio recordings were being made. In another example, if the invention is used as on open air collector to detect sound across a long distance during a live event (such as a sporting event), the camera can be used to simultaneously record video of event.

The microphone end 35 of hollow tube 37—and hollow tube 37 itself—are incorporated with casing 31, and can be cast in the same mold, or printed by the same 3D printer. Hollow tube 37 curves and runs along the back of casing 31 toward the center of the casing.

FIG. 1B shows embodiment 30 provided with an embedded acoustic collector 44, which, like the hollow tube 37, can be cast in the same mold as casing 31, or printed on the same 3D printer. When the collector is cast from the same mold as the casing, or printed on the same 3D printer, or otherwise manufactured as permanently affixed to the casing, the collector will be referred to as "incorporated with the casing."

As a general matter, any funnel-like structure can serve as an acoustic collector for both stethoscope and longer-range sound collection purposes. As will be described, the collector 44 shown here is specially configured to be used as a stethoscope chestpiece, though could also be used for longer-range sound collection. FIGS. 8A-8C, by comparison, depict an alternative embodiment in which the collector is specifically intended for long-range, open air sound collection.

Returning to FIG. 1B, the hollow tube 37 runs along the back of casing 31 and opens at hole 45 of embedded collector 44. The embedded collector 44 has a sloped inner wall 41 that extends outward from hole 45. Embedded collector 44 is provided with a grooved or threaded outer rim 43 for mounting a diaphragm or other circular attachments, such as a rubberized O-ring. As such, collector 44 is specially designed to be used as a stethoscope chestpiece (though could also be used for longer-range open air sound collection).

When designed to mount a diaphragm, collector 44 is preferably constructed of a rigid material such as hard plastic or metal. However, when used on its own as a stethoscope chestpiece without a diaphragm, it will be advantageous to construct the collector 44 from a flexible rubber material that can deform to match the contours of the surface being listened to such that it forms a good seal. Alternatively, the lip 43 can be fitted with a flexible rubber sealing ring to accomplish the same purpose, as discussed further below.

FIG. 1C is a side view of the exterior of embodiment 30, shown here on its own without the device 33. An opening 57 is provided for buttons along the side of device 33. Similar openings may be placed wherever necessary to access the surface of the device 33. Hollow tube 37 is shown running along the back surface of casing 31, with embedded collector 44 protruding outward.

FIG. 1D is a cross-sectional view of embodiment 30. The inner backing 55 of casing 31 would be substantially flush against the back of the device 33 when the casing is attached to the device. Similarly, upper lip 68 of lip 32 would partially overlap the front face 32A of the device 33, thereby hooking onto the device 33 in conjunction with the side portions of lip 32. Hollow tube 37 (from FIG. 1B) is shown as having a hollow core 53 that runs from collector hole 45 to the microphone end opening 34.

The embedded collector 44 (from FIG. 1C) may be constructed with a hollow chamber 51 behind sloped inner wall 41. This design will decrease the quantity of material in (and therefore the weight of) the casing. Hollow chamber 51 can be filled with materials having certain sound dampening/transmission properties to suit the particular application of the stethoscope chestpiece.

FIG. 1D depicts embedded collector 44 with a grooved rim 43. This rim can serve multiple purposes. In one mode, it can be designed as the attachment point for a rigid circular collar 62 that mounts a diaphragm 64. Screw threading can be added to rim 43 for mounting collars with corresponding threading. Alternatively, a collar may be provided capable of snap-fitting over rim 43. Rim 43 can also serve as the mounting point for an elastic O-ring, also used for attachment of a diaphragm.

As a practical matter, many modern stethoscope chestpiece diaphragms are about 1.7 inches in diameter. For example, the ubiquitous Littmann brand stethoscopes (manufactured by 3M), traditionally have chestpieces with diameters of about 1.7 inches. It will thus be advantageous to design collector 44 to accommodate diaphragms having that dimension (assuming it is intended to be used as a stethoscope chestpiece).

Depending on the use the collector is being put to, collector 44 need not be fitted with a diaphragm. For example, collector 44 can be used as a bell for detecting lower frequency sounds. Its use as a bell will be improved by fitting rim 43 with a rubberized ring for creating a seal over the listening surface. As noted, collector 44 can also be used as a longer-range sound collector. For example, a hearing impaired person might use collector 44 to collect and amplify sound across a room. An attendee at a live performance or sporting event might also use collector 44 to amplify sound over a longer distance.

Although embodiments of the invention have thus far been shown with the collector located on the broad surface of the casing, the casing may also be designed with the collector located in any of a variety of other positions. For instance, the collector may be attached to the edge of the case, acoustically coupled directly with the device's microphone. The size of the collector may vary depending on the size of the device it is being coupled with. If the collector is attached to the edge of the device, the size of the attachment will be in congruence with the size of the device's edge.

It should also be noted that in the above-described embodiments, and in the embodiments that follow, it will be advantageous to design the opening of the hollow tube over the microphone to have a rubberized or gel sealing ring that can be compressed by the casing to form a tight seal between the tube and the microphone. This added seal will help improve audio transmission quality.

It should additionally be noted that embodiments of the invention can operate with the acoustic collector physically separate and independently moveable from the casing, with a length of flexible tubing connecting the collector to the handheld device's microphone. This is in contrast to the embodiments depicted in the Figures, which show the collector affixed to the casing, either because it is directly bonded (i.e., incorporated with) with the casing, or detachably mounted in such a way that any independent movement is substantially restricted. For example, the collector 81 of embodiment 70 in FIG. 3 is still deemed "affixed" to a casing 72 because a neck 73 can be made rigid with respect to the casing 72 such that the collector 81 does not move freely from the casing 72.

While the figures herein depict tubing as embedded within the casing, the tubing could just as easily be fixed to the outside of the casing. As a practical matter it may be easier to manufacture the casing with the tubing as an embedded channel, which also reduces the extent to which the tube projects out from the side of the casing. Whether embedded or attached to the outside of the casing, such rigidly fixed tubing may be referred to herein is as "fixed" to the casing (as opposed to extending away from the casing as an independent component).

FIG. 3 depicts an alternative embodiment 70 of the invention designed to allow easy mounting of a collector having a stem. Because many stethoscope chestpieces have stems, embodiment 70 is particularly suited to use with such chestpieces, though it could also be used with an open air collector having a stem (or, as discussed below, with any collector that can be attached to the device by other means).

Here, the casing 72 is provided much like casing 31 (from FIG. 1A). Just as in embodiment 30 (of FIG. 1A), a hollow tube 78 is incorporated with the casing, and runs to a microphone end 76 opening over the recording microphone aperture of the handheld electronic device. Here, however, the hollow tube 78 bends around juncture 73 and curves outward and upward to form neck 75.

The juncture 73 and neck 75 may be made of a relatively stiff material, such as rigid polymeric material or the like, such that it will tend to hold the chestpiece securely. The chestpiece is thereby prevented from pivoting relative to the casing. Alternatively, the juncture 73 may be provided with a pivot joint 71 that allows the neck 75 to pivot relative to the casing 72. The joint could be designed to have sufficient friction that it will tend to remain in a given position unless moved by the user. Alternatively, the joint 71 could be provided with a screw that can be loosed to pivot neck 75 and then tightened to hold it in place.

In an alternative embodiment (not shown) the collector might be directly attached to the casing by a pivot joint such as a ball and socket joint that allows the collector to pivot relative to the casing. In such an embodiment, each of the ball and socket would have a hole to allow the transmission of sound to the tubing that runs to the electronic device's microphone. The hole openings in the ball and the socket would have to be wide enough such that an air passage can be maintained between the ball and socket even if the collector is pivoted.

As shown in the particular embodiment depicted in FIG. 3, neck 75 is designed to be wide enough to accommodate most stethoscope chestpiece stems, which typically are less than a half inch in diameter. The design would of course work with an open air collector having a similar stem diameter, or the neck 75 could be designed to have whatever diameter is called for by the user's application. A rubberized mating washer 77 may be provided to improve the seal and grip around stem 79 of collector 81. The washer 77 may be made of a rubberized material with a relatively narrow opening capable of elastically expanding to accommodate and securely grip stem 79. Alternatively, removable washers of various sizes may be provided with the device for mounting collectors with stems having different diameters. Embodiment 70 thus enables users to supply their own collector, and modify the mounting system to conform to the user's selection.

Having a neck-and-stem system has the added advantage of allowing the collector 81 to rotate within the neck 75 to whatever angle is desired by the user. Alternatively, embodiment 70 could be designed with the collector permanently incorporated with the neck, and if rotational pivoting is desired, a rotatry joint could be added to neck 75. As with pivot joint 71, the rotary joint could be designed to have sufficient friction that it will tend to stay in a given position unless moved by the user.

FIG. 4A is a side view of a system 90 for directly mounting a collector to a casing 87. Here, the casing (shown in cross-section) is provided with an embedded hollow tube with hollow core 89, like hollow core 53 (in FIG. 10). A raised slot 85 is provided on the surface of casing 87 for mounting the pinched end 95 of collector 97. The opening of slot 85 is just wide enough to accommodate the pinched neck 99 of collector 97. The pinched end 95 of collector 97 fills a correspondingly shaped cavity 91 within slot 85. End 95 is provided with a rubberized tip 93 to form a seal with the inner walls of cavity 91 about the hollow core opening 89.

FIG. 4B is a plan view of the mounting system 90 (of FIG. 4A). Raised slot 85 is shown with dotted lines indicating inner cavity 91. Collector 97 is shown with dotted lines representing pinched neck 99 and pinched end 95 on the opposite side of the collector facing casing 87. With reference to FIGS. 4B and 4A, the user can mount the collector 97 to the casing 87 by sliding the pinched end 95 into the cavity 91 of slot 85. Rubberized tip 93 can be made slightly larger than the cavity space so that it will elastically compress and form a tight seal that will help conduct sound and prevent the collector from disconnecting from the casing.

Figure 5:
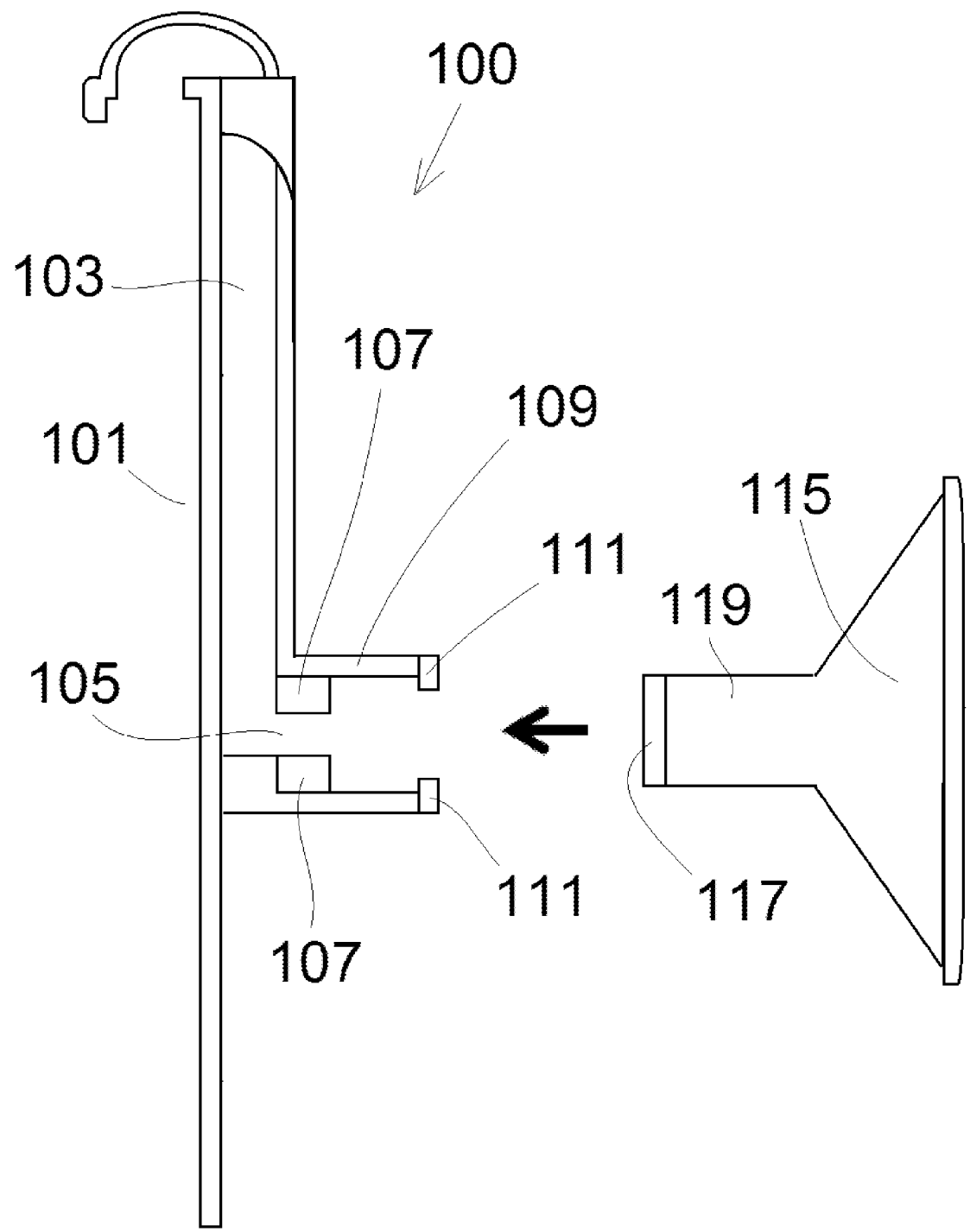
FIG. 5 is a side cross-sectional view of an embodiment of the present invention.

FIG. 5 depicts another embodiment 100 of the present invention featuring an alternative mounting system. Here, a casing 101 (shown in cross-section) is provided similar to casing 31 (in FIG. 1A). A hollow tube with hollow core 103 runs to an opening 105 on the back of the casing 101. Here, a substantially rigid neck 109 is provided for mounting a corresponding stem 119 of collector 115. A rubberized ring 111 encircles the tip of neck 109 and provides a tight seal for stem 119.

Neck 109 may also be provided with magnetic portions 107 for attaching to a corresponding magnet or ferromagnetic material 117 at the tip of stem 119. If magnets are used, they should be selected to have a level of intensity such that, depending on their location relative to the handheld electronic device and the type of electronic device used, the magnets will not interfere with the function of the electronic device. The selection of magnets will thus depend on the technical parameters of the handheld electronic device being used with embodiment 100.

Figure 6A:
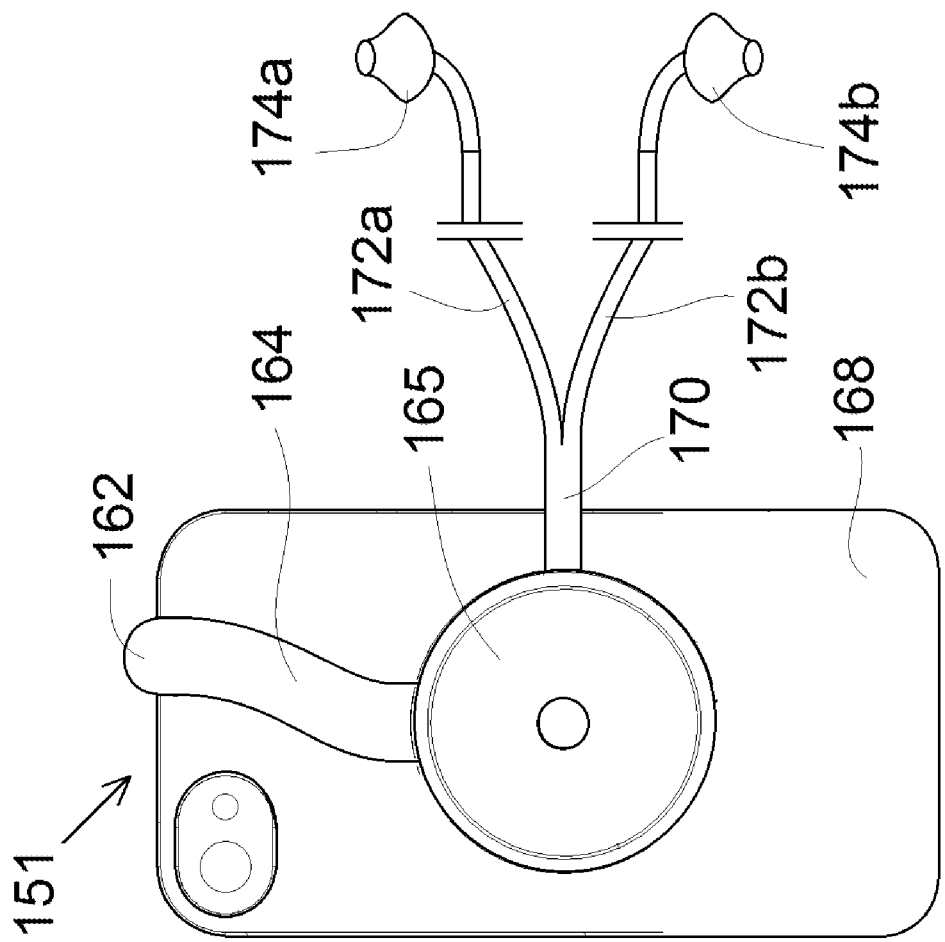
FIG. 6A is a plan view of another embodiment of the present invention.

FIG. 6A depicts an alternative embodiment 150 of the invention. Here, a casing 158 has been designed to cover the entire backing of the handheld electronic device (rather than just the upper portion as in previous embodiments). In this regard, the casing 158 is much like standard protective casings currently sold by companies such as Incase as accessories to smartphones.

A hollow tube 154 is embedded along an angle in the casing 158 (rather than with 90 degree joints as previously shown). It should be noted that although the invention can be used with angled tubing such as that shown in previous figures, it is preferred to have tubing that runs along the shortest distance with the fewest bends. The shorter the tubing and the fewer bends it has, the better the sound transmission.

Also included in embodiment 150 is a second tubing 156 branching off of a collector 155. This second tubing 156 terminates in an open end 160 that covers a second microphone on the opposite side of the device. In this manner, the embodiment 150 is capable of delivering sound to two different microphones, even if only one is used at a time.

Figure 6B:
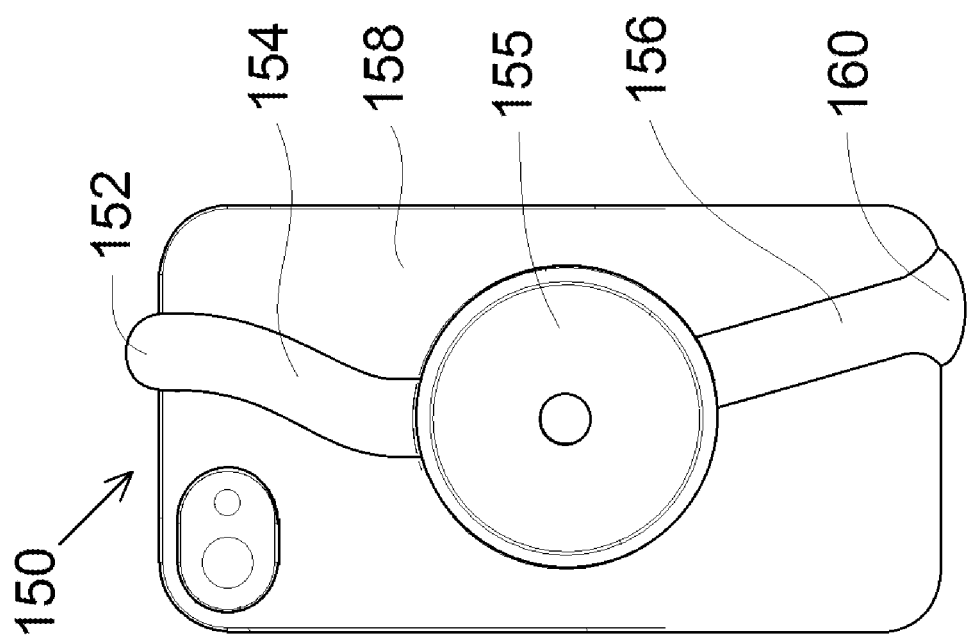
FIG. 6B is a plan view of another embodiment of the present invention.

FIG. 6B depicts an alternative embodiment 151 of the invention which has a first tube 164 running to the handheld device's microphone, as well as a second branching tube 170 that extends beyond the casing 168 and splits into ear channels 172a and 172b. These ear channels function like those of conventional stethoscopes and terminate in ear buds 174a and 174b. Note that the full length of ear channels 172a and 172b has been truncated here for illustrative purposes. Embodiment 151 allows the user to listen to the stethoscope at the same time as the handheld device's microphone registers the sounds it conducts.

It should be noted that the branching second tube 170 could just as easily be connected to a different form of listening device, such as a second microphone. This second microphone could also in turn be paired with a recording device or speaker that is physically separate from the main handheld device.

FIGS. 7A and 7B show yet another alternative embodiment 180 of the invention that eliminates the casing and replaces it with a band 187 that encircles a handheld electronic device 183. Band 187 is preferably elastic and sized to tightly wrap around the device 183. Alternatively, band 187 may be equipped with a commonplace length adjuster—such as a notched belt buckle, or Velcro ends (not shown)—that allow the user to wrap it around device 183 with a desired tightness.

Included with belt 187 is a microphone mounting port 193 that allows attachment of a hollow collector tube 181. The port 193 is preferably made of rigid hollow plastic, and the tube 181 is preferably made of a rubber-like material having sufficient elasticity to mate with port 193 as shown in FIG. 7B. A port base 191—included with the belt 187—has a rubber seal for forming a sealed connection with the microphone on device 183.

Rather than employing a mounting port 193, the port might alternatively feature a magnetic ring, and the corresponding end of tube 181 provided with a mating magnetic ring. Thus, the paired ring magnets would hold the end of tube 181 directly over the microphone port by the force of magnetic attraction.

A collector may be incorporated directly into belt 187, with tube 181 running from the collector to the port 193. When it is desired to use the invention as a stethoscope, the embodiment 180 can also take advantage of the fact that many chestpieces have bulbous ends, and use one or the other of those bulbous ends to secure the chestpiece to the belt 187. FIG. 7B shows a chestpiece 189 having a bulbous bell 185. Belt 187 is equipped with a fitting 192 for grabbing bell 185 and holding it fixed against belt 187. Additional padding may be added to the portion of belt 187 that contacts the chestpiece to reduce sound conduction directly into the device 183.

The fitting 192 is preferably an elastic band with a hole having a diameter similar to the diameter of the central portion 194 of chestpiece 189. The user can stretch open the elastic hole of fitting 192 to accommodate bell 185. In this case, the length of fitting 192 should be such that it elastically holds bell 185 tightly to belt 187.

Embodiment 180 thus advantageously allows the user to employ a wide range of stethoscope chestpieces and tubing of the user's selection, and does not require selling the chestpiece with the device.

FIGS. 8A, 8B, and 8C depict an alternative embodiment 200 of the invention specially designed to be used as a contactless, longer-range sound collector, i.e., and "open air" collector. FIG. 8A depicts a handheld electronic device casing 203 (in this case, similar to a standard iPhone casing). Directly attached to that casing is a parabolic sound collector dish 207 which has a parabolically sloped inner wall 211. A rigid focal point tube 205 extends across the valley created by the parabolically sloped inner wall 211 and opens to funnel 209 located at the geometric focal point of the parabola. The geometric focal point is the location at which the collector dish 207 will concentrate sound waves. Focal point tube 205 connects with embedded casing tube 202, which terminates at microphone end 201 over the device's microphone.

FIG. 8B is a side view of embodiment 200 showing how the focal point tube 205 traverses the opening of collector dish 207. FIG. 8C is a cross-sectional view of FIG. 8B that shows the parabolic curve of inner wall 211. With reference to FIGS. 8A, 8B, and 8C, focal point tube 205 opens at funnel opening 209a of funnel end 209. Funnel 209 collects the sound that is reflected to the focal point of parabolic inner wall 207. Those sound waves are then transmitted through the tubing channel 215 to microphone end 201. Lips 213 and 217 of casing 203 hook onto the handheld electronic device (not shown), and keep the embodiment 200 securely attached to it.

Though not shown in the drawings, it is also possible for the collector dish and focal point tubing to be a separate unit capable of moving independently from the handheld electronic device and connected to the handheld electronic device via a length of flexible tubing. Such an embodiment would allow larger collector dishes to be used as they could be supported by the user's hand rather relying solely on the support of the casing.

A test was performed using a device casing and collector similar to that shown in FIGS. 1A-1D. First, an iPhone (model 4S) was placed at approximately 14 feet from a constant sound source. A comparison was made between the sound registered by the iPhone without the invention attached and with the invention attached. When the invention was attached, a marked increase in volume was observed.

Turning now to FIG. 9A, another embodiment of the invention is depicted in which a chestpiece 250 is separable from a device casing 275 (shown in FIG. 9D). In FIG. 9A, the sound-collecting face of the chestpiece 250 is facing away (out the back of the page) with a flat back surface 250a exposed. Along the perimeter of back surface 250a are a series of structures designed for mating with corresponding strictures on wave guide tube 257 shown in FIG. 9B. Wave guide tube 257 is substantially circular in cross-section, and has a series of openings 255a-f cut into one of its sides. Referring to FIGS. 9A and 9B, a hole 252a is exposed and surrounded by a lip 252 which is capable of being inserted into any of the openings 255a-f on wave guide tube 257. The structures 253a-e are curved coverings that project from the back surface 250a of chestpiece 250, and these coverings are capable of sealing the openings 255a-e on wave guide tube 257 such that it becomes a fully sealed hollow tube.

It should be noted that various terms such as "waveguide," "tube," "passageway," and "cavity" are used herein to describe the hollow air passage connecting the chestpiece to the electronic device's microphone. Each of these is a species of, and may be referred to generically as, "hollow passages."

Referring now to FIG. 9C, the sealing action of the structures on back surface 250a with relation to the openings in wave guide tube 257 is shown conceptually via a cutaway drawing. The cross-section of the openings 255f and 255e in wave guide tube 257 are semicircular in this example, and permit the insertion of lip 252 and structure 253e, respectively. Lip 252 opens inward into the back surface 250a of chestpiece 250 through hole 252a. Lip 252 has projection 252b which serves to seal off the portion of wave guide tube 257 to the left of hole 252a. Note that the portion of the tube to the right of hole 252a remains clear. Structure 253e acts to seal off opening 255e, thereby creating a sealed hollow tube. A thin coating of rubberized material or foam about the openings 255a-f will help to create a snug seal between the components. The portion of the tube 257 through which sound is to be conducted to a microphone will be referred to as the proximal portion, while the portion that is sealed off by projection 252b will be referred to as the distal portion.

With reference to FIGS. 9A, 9B, and 9C, it will be appreciated that when lip 252 is inserted into opening 255f, the remaining openings 255a-e with be sealed off by structures 253a-e, respectively. Air passing from hole 252a into the wave guide tube 257 will have to travel the entire length of the tube to exit. If the chestpiece 250 is rotated with respect to the tube 257 and lip 252 is inserted, for example, into opening 255c, then projection 252b will serve to seal off the portion of the tube 257 inhabited by openings 255d, 255e and 255f. Air entering the tube 257 through hole 252a will now have a shorter distance to travel to exit the tube.

Turning now to FIGS. 9D and 9E, a complete assemblage of an embodiment of the invention is shown in cross-section. Chestpiece 250 has an aperture 260 for collecting sound into a tube that opens out at hole 252a. The electronic device casing 275 is designed to accommodate a portable electronic device against its back surface 275c, and pinched between upper and lower lips 275a and 275b. Wave guide tube 257 merges into tube 262 which exits at opening 262a over the electronic device's microphone.

The user of the device casing inserts chestpiece into the opening bounded by sides 278a and 278b of receptacle 278. Backstops 277a and 277b prevent chestpiece 250 from sliding too far into the device casing. When oriented as shown in the Figures, lip 252a and projection 252b will be inserted into opening 255f in wave guide tube 257. This will act to effectively lock chestpiece 250 into device casing 275. A coating of rubberized material or foam along the inner surface of receptacle 278 will serve to create friction to help seal chestpiece 250 into place. The friction should be sufficient to lock the chestpiece in place during normal use, yet allow the user to apply force to remove the chestpiece when desired. FIG. 9E depicts the device with the chestpiece fully inserted.

With reference to FIGS. 9A-9E, it will be appreciated that the user can easily modify the effective length of the wave guide tube 257 by removing the chestpiece, rotating it, and the re-inserting it in the desired position such that hole 252a lines up over the desired one of the openings 255a-f. Varying the length of the wave guide tube in this manner will allow the user to change the acoustic properties of the sound received by the electronic device's microphone at opening 262a. By making the wave guide tube longer or shorter, the user will preferentially diminish certain wavelengths of sound while allowing others to propagate more freely. This procedure is advantageous when the user is trying to enhance collection of certain wavelengths of sounds.

Figure 10D:
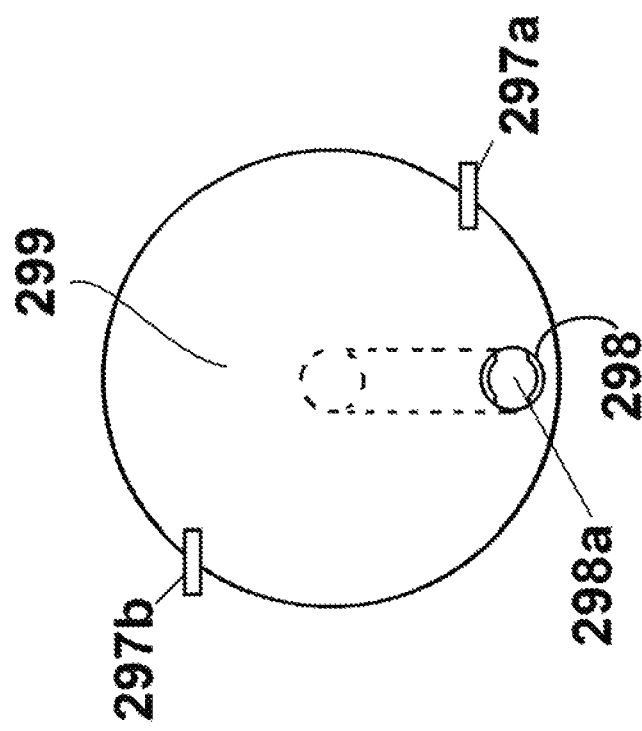
FIG. 10D is a plan view of a component of the device depicted in FIGS. 10A and 10B.
Figure 10C:
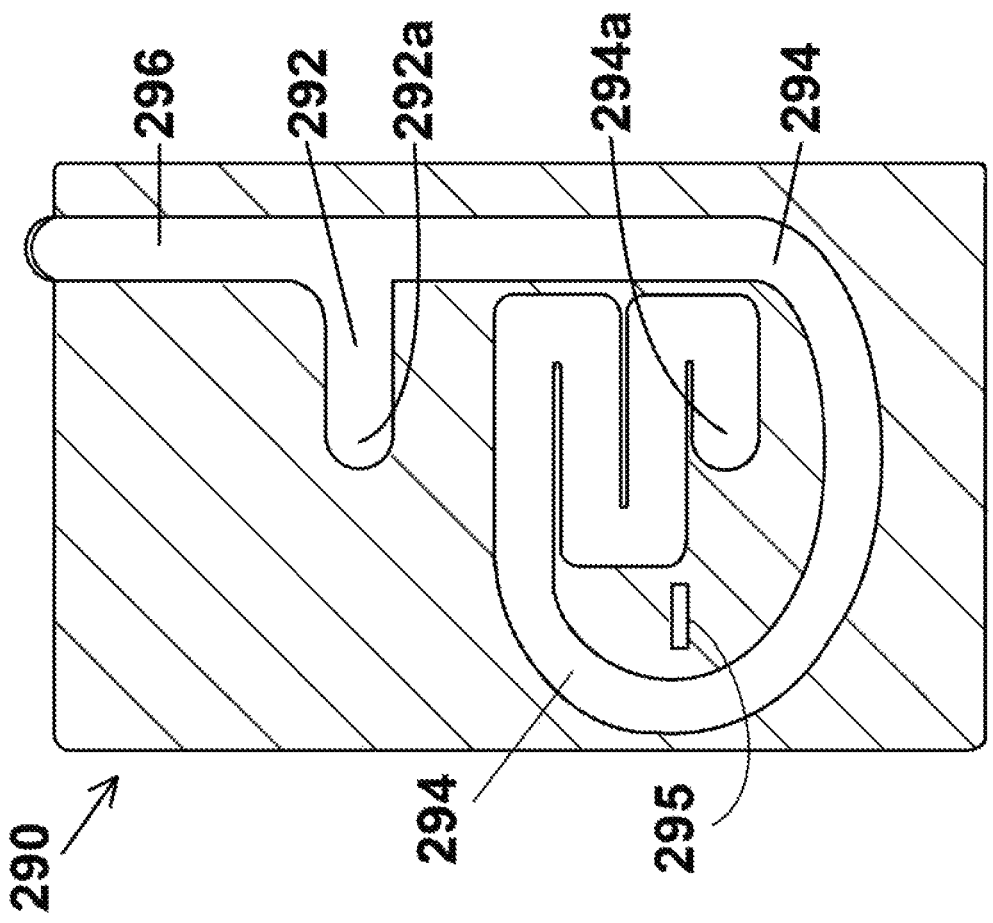
FIG. 10C is a frontal cross-sectional view of the device depicted in FIGS. 10A and 10B.

A similar objective is achieved by the device depicted in FIGS. 10A-10D. Referring to FIGS. 10A and 10B, a device similar to the one in FIGS. 9D and 9E is shown. Electronic device casing 300 is shown cut in a cross-section. Chestpiece 299 (also in cross-section) has an aperture 299a that collects sound into a tube that runs to a hole 298a bounded by lips 298. Here, as is shown in FIG. 10C, the device casing has two wave guide tube passageways 292 and 294. In FIGS. 10A and 10B, the lips 298 are shown inserted into opening 294a of wave guide passageway 294. However, the user can separate the chestpiece 299 from the device casing 300, rotate it, and re-insert it with lips 298 inserted into opening 292a of wave guide passageway 292. Sides 302a and 302b of receptacle 302 function in substantially the same manner as sides 278a and 278b in FIG. 9D.

Referring now to FIG. 10C, a cross-section of device casing 300 (of FIG. 10A) is shown revealing the structure of the wave guide passageways 294 and 292. As can be seen, passageway 292 is short, and leads right into tube 296a, which contains passageway 296. Passageway 294, however, is long and coiled. When the chestpiece is oriented such that lips 298 are inserted into opening 294a, air passing from hole 298a in the chestpiece into the device casing will have a longer and more tortuous distance to travel to reach the electronic device's microphone. When the chestpiece 299 is inserted with the lips 298 inserted into opening 292a, the distance is significantly shortened.

FIG. 10D depicts the flat back surface of chestpiece 299 with lips 298 projecting out of the page. Slat projection 297a projects outward from the surface. With reference to FIGS. 10A-10D, at the juncture of passageways 294 and 292 is an opening (not shown in the cross-section) in the tubing of passageway 294. This opening allows for the insertion of slat projection 297a when the chestpiece is oriented such that lips 298 are inserted into opening 292a. In this orientation, air will flow from the chestpiece through hole 298a into opening 292a and then into passageway 296. Slat projection 297a will act to seal off passageway 294, preventing air from traveling in that direction. The portion of the passageway through which sound is to be conducted to a microphone will be referred to as the proximal portion, while the portion that is sealed off by projection 297a will be referred to as the distal portion.

When the chestpiece 299 is oriented such that lips 298 are inserted into opening 294, slat projection 297a will slide into slot 295. At the same time, sealing structure 297b—which is matched to the shape of the opening in passageway 294 that slat projection 297a would otherwise have occupied—acts to cover that opening so that the walls of pathway 294 are contiguous and sealed.

The embodiments depicted in FIGS. 9A-10D are intended to be merely representative of the wide variety of possible configurations that may be achieved applying similar design strategies. Any number of sizes and shapes of wave guide tubes and pathways might be achieved, and selected for their particular usefulness in filtering or augmenting certain kinds of sounds, or certain acoustic wavelengths. The embodiments shown in FIGS. 9A-10D show how such variation can be achieved using a separable chestpiece and a fixed wave guide tube/pathway.

When pressed against a surface, the chestpiece may tend to pick up undesired sound frequencies. For example, when used as a stethoscope, the chestpiece may pick up ambient noise and rustling from its contract with cloths and skin. These sounds tend have to at a higher frequency that of the heart and other biological sounds. One way to help amplify the desired frequencies so that they come through louder than the undesired frequencies is to employ one or more resonators in conjunction (or as part of) the hollow passage. A resonator is a material that is pre-designed to preferentially vibrate at a certain frequency. Thus, if a portion of the hollow passage is formed from a material that tends to resonate at the desired frequency, it will amplify the sound of that frequency as it passes through the resonant zone. Such resonators might be formed as part of the main hollow passage itself, or as hollow side branches from the main hollow passage. The resonance of the resonator material can be controlled not only by choice of the material, but by the thickness and shape of its construction.

While it is desirable that sound be conducted with sufficient volume through the hollow passage, it is undesirable for the device casing to vibrate relative to the device, as this causes sound distortion. Thus, it is advantageous to dampen such vibration by using an acoustic absorbent layer at the interface with the device to which the casing is attached. This layer might be formed of materials such as foam, nyoprene, silicone, cork, or fabric, and can be attached to the external surface of the casing where it interfaces with the electronic device. This absorbent material will also help with achieving a tighter fit. Similarly, the same kinds of sound dampening materials may be affixed to the casing along its external surface on top of the hollow passage to prevent transmission of sound and vibration between the hollow passage and the external environment.

Microphone Systems

In another embodiment of the invention, a miniature microphone may be placed within the hollow passage extending from the aperture of the chestpiece. Referring to FIGS. 11A and 11B, an example of such an embodiment is shown. In FIG. 11A, fitted device casing 325 is shown in cross-section not yet mounted to an electronic device. If the electronic device were to be inserted, it would rest against the casing back 324, and be clasped by lip 311.

Figure 11C:
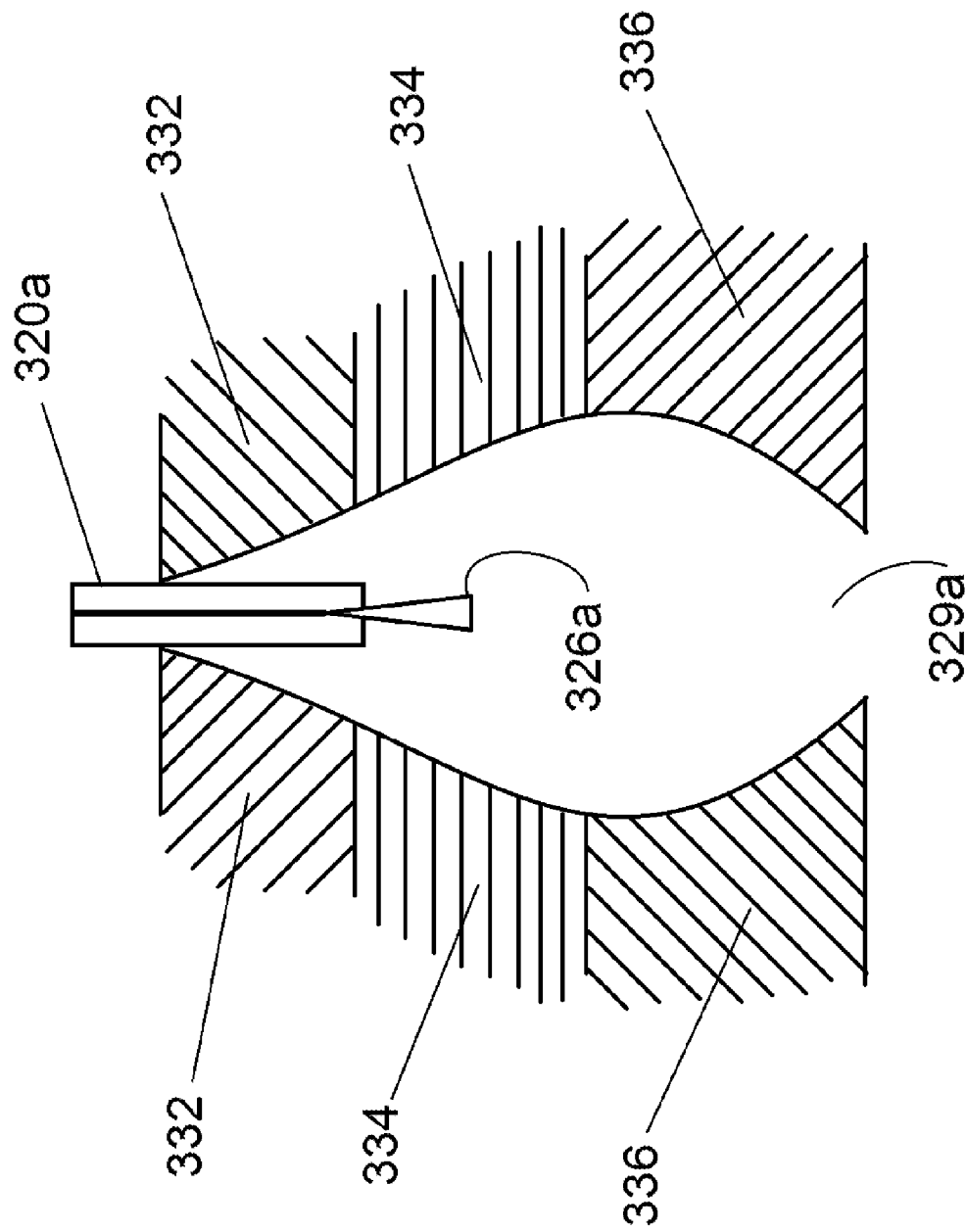
FIG. 11C is a cross-sectional view of a portion of the interior of an embodiment of the present invention.

The casing 325 has a chestpiece 330 with an aperture hole 328 for admitting sound waves. The sound waves are then conducted through the hollow passage, or wave guide, 329. In the particular embodiment shown, the passage has a largely uniform circular cross-section, as shown by the dashed lines in FIG. 11B (which is an exterior plan view of the front of the casing 325 from FIG. 11A). However, the wave guide passage 329 may take on any number of shapes depending on the desired application. For example, by making the wave guide passage larger, longer wavelength sounds will be more easily transmitted and will be reverberated through a wider chamber. If the passage is made smaller, the range of frequencies and volume of sounds passing through will be diminished. FIG. 11C, for example, shows a cross-sectional cut-away of a passage 329a of varied width.

With reference to FIGS. 11A and 11B, inserted within passage 329 is a microphone 326 mounted within a plug 320. As showed here, the plug 320 is fitted to the passage 329 such that it forms a tight seal around its edges. Plug 320 serves both to mount the microphone 326 and to deaden vibration reaching the microphone 326 from the sides or behind. For this purpose, plug 320 may be made of a foam or rubberized material with low sound conduction properties. Preferably, plug 320 is sized to fit snuggly within passage 329 such that it will maintain its position within passage 329 during normal use, but may be withdrawn or re-positioned within passage 329 by the user when desired. Constructing plug 320 of compressible foam is one way to achieve this objective. Tracks or notches may also be employed to fix the position of plug 320 within passage 329. A handle 318 mounted to plug 320 may be employed to aid the user with manipulating plug 320 within passage 329.

While it will be preferred in most anticipated applications that the plug be substantially matched in size to the diameter of the passage, the term "plug" as used herein might also refer to a thinner structure of a diameter less than that of the passage, or even a very thin structure for mounting the microphone, like a bendable wire. Which type of plug is used will depend on the sound quality requirements of the application.

In various embodiments, the size of passage 329 may be varied by the user by manipulating how far plug 320 is inserted. As shown in FIG. 11A, the distance D between the microphone 326 and the chestpiece aperture 328 may be varied. This in turn changes the size of the passage 329, which changes the properties of the sound conducted.

Referring to the cross-sectional cut-away of FIG. 11C (which is unrelated to FIGS. 11A and 11B), if the passage 329a has a varied width with wider and narrower cavity portions, or if the walls of the passage 329a have varied sound conduction/resonance properties along the passage's length (such as different materials that reflect, absorb or resonate sound to a different degree), then changing the position of microphone 326a relative to those different portions of passage 329a would act to adjust the properties of the sound transmitted to the microphone 326a. FIG. 11C depicts both a varied width passage and passage walls made from differing materials. In this hypothetical example, a first material 332 having a relatively high sound-reflective surface forms the walls of the upper portion of the wave guide cavity 329a. A second material 334 having a relatively high sound-dampening quality makes up the walls in the middle portion of the passage 329a, and a third material 336 having a moderate sound-reflective surface forms the lower walls. By varying the position of the microphone 326a relative to these wall surfaces, the user can manipulate the quality of sound recorded. Of course, the passage 329a need not vary in both length and material type. If, for example, all that is desired is the ability to vary between dampened and highly reflected sound, such could be accomplished by having the proximal portion of the passage constructed of sound absorbing material, and the distal end composed of sound-reflective material, without varying the width of the passage.

Though not shown in the drawings, it is also possible for the device casing's air passage to have a curved shape, and if the microphone plug is flexible, it can be made to follow that curved path by applying pressure to its proximal end.

Referring back to FIG. 11A, the microphone wire 316 exits the plug 320 and runs to a jack 314 for insertion into the electronic device (not shown). A port 312 in the top of the device casing 325 serves to mount the jack 314. It is also possible to power the microphone by a battery in the plug 320 (not shown) and to employ a wireless transmitter to send the microphone recordings to the electronic device.

The pairing of the microphone with a waveguide passage is particularly useful since the sound frequencies may be filtered by the passage (and any accompanying resonators) as they reach the microphone.

The microphone itself maybe designed as either directional or omnidirectional depending on the particular application. If it is desired to receive only those sound waves transmitted along the length of the passage perpendicular to the microphone, it will be preferable to use a directional microphone. The plug itself will enhance the directional quality of sound recording by limiting vibrations received behind and to the side of the microphone. Of course, if it is desired to place the microphone in an open cavity such that it can gather sound from all directions, an omnidirectional microphone can be used and the plug can be designed to expose all sides of the microphone. Such an embodiment is contemplated in FIG. 11C, where the omnidirectional microphone 326a extends away from the plug 320a.

Various types of miniature microphones are well known in the art, and are already used with handheld electronic equipment. A particular type of directional microphone that may be of unique benefit to the present invention was recently developed at the State University of New York and is described in U.S. Pat. No. 6,963,653. This microphone uses miniature pivoting diaphragms to isolate sounds coming from a particular direction, and has been proposed to be used in hearing aids. The same technology could also be adapted for use with the devices disclosed herein to achieve enhanced directional recording ability.

EKG System

It is also possible to couple the present invention with an electrocardiogram (EKG) recording system. As shown in FIG. 11B, three EKG leads 337 may be spaced apart from one another about the perimeter of the chestpiece. These leads may be connected via wiring running through the casing. When placed against the chest, the EKG leads can record the electrical impulses of the heart, and transmit these either via a wired connection to the electronic device to which the case is attached, or to an intermediate unit that can re-transmit the EKG signal wirelessly, such as by Bluetooth or other near range signal.

If it is desired to use a wired connection to the electronic device to receive both an EKG signal and a microphone signal, the two signals can be transmitted through the same jack by encoding both signals on the same carrier wave. This could be done, for example, by frequency-shift-keying (FSK) that sends bytes of data alternating between the data sources, or by encoding the data sources on the same carrier wave simultaneously by encoding one through a frequency-modulation (FM) method and one through an amplitude-modulation (AM) method. This could also be achieved by encoding the inputs in the same way stereo sound in encoded on FM radio waves for regular radios: the main carrier wave encodes the sum of the left and right signals, and a subcarrier encodes the difference between the left and right signals. This is then decoded at the receiving end. Essentially, the microphone data can be encoded in order to allow for other signals to be transmitted to the phone along the same input line.

Varieties of Handheld Electronic Devices

While the drawings herein depict a casing used with an electronic device similar to an early model iPhone, it should be understood that embodiments of the present invention can be used with a wide variety of handheld electronic devices such as tablets, smartphones, cellular phones and the like. Embodiments of the invention might also be used with any number of other handheld electronic devices of any shape by using the same lips and attachment means disclosed herein.

As used herein, "handheld electronic device" specifically includes (but is not limited to) iPhones (and similar devices), iPads (and similar devices), tablets, smartphones, iPods equipped with microphones (and similar devices), and mobile telephones. "Smartphone" refers to any wireless phone having a generally flat, rectangular shape, such as an Apple iPhone or Samsung Galaxy phone (as well as any similar-functioning, flat handheld devices that may yet come to market not having a rectangular shape). "Tablet" refers to any microphone-equipped handheld electronic device that has a generally flat, rectangular shape, but which may not be equipped with a telephone feature (as well as any similar-functioning, flat handheld devices that may yet come to market not having a rectangular shape). Tablets include, for example, the Apple iPad, the Barnes & Noble Nook, and the Microsoft Surface. The term "Smartphone/Tablet" encompasses both of those terms as just defined.

According to embodiments of the present invention, an acoustic collector may be mounted to such handheld electronic devices by providing a fitted casing that is capable of wrapping around at least a portion of the device and hooking onto it (as discussed above), with a hollow audio tube connected to the casing and positioned over the device's microphone.

It is also possible that a casing could be made to attach to a handheld electronic device without hooking onto it as shown in FIGS. 2B-2D. For example, the embodiments shown in FIGS. 1A-1D could be functional without lip 32. One way this could be accomplished is by using a magnetic attachment means to hold the casing to the electronic device. For example, small magnets could be embedded within the edges of the casing that tend to attract the corresponding edges of the electronic device. Or a magnet could be embedded with the broad portion of the casing. Wherever magnets are used throughout this disclosure, care should be taken to investigate whether the particular electronic device being used might be disrupted by magnetic fields in certain locations. Devices such as the iPad are known to employ magnets along their edges without disruption of the functioning of the device. Alternatively, if it is desired not to use either lips or magnets, the user could simply "pinch" the casing to the electronic device while it is in use to ensure that the casing does not become dislodged.

It should be noted that it is advantageous to be able to use the present invention with a speaker so that the user can listen to the sounds conducted through the stethoscope at the same time as those sounds are being received by the electronic device's microphone. Most Smartphone/Tablets include their own speakers that can provide such simultaneous sound projection. Feedback effects can be minimized by ensuring a tight seal around the microphone. Additionally, software applications are available that reduce microphone feedback.

Alternatively, as shown in FIG. 6B, a secondary tubing can branch from the device and be connected to a separate listening instrument. That instrument can be a separate microphone and speaker system for projecting the sounds conducted by the stethoscope. Providing a separate speaker unit of this kind will allow the sounds to be projected in a separate location, and will minimize feedback effects.

Applicants note that Smartphone/Tablet devices may yet come to market that are made of thin, flexible material, allowing them to bend or even roll up like paper. It has already been proposed to introduce such products using OLED technology. The present invention can be adapted to work with such thin, flexible devices by providing a rigid or semi-rigid casing that covers most or all of the device, and which has one or more padded lips that can be tightened about an edge (or edges) of the flexible device. For example, a clipboard-type clamping mechanism can be incorporated into the casing lip to clamp an edge of the flexible device. Alternatively, the casing could be designed with edge lips that hook onto opposite sides of the flexible device, and a chord could be extended from opposite sides of the casing across the face of the device to hold it into the casing. Rather than using lips, the casing might include one or more suction cups for attachment to the flexible device. To the extent the flexible device has a metallic component, magnets could also be used to affix the device to the casing.

Alternatively, a casing could be provided with a central slot, allowing all or part of the flexible Smartphone/Tablet device to slide into the casing and be held rigidly therein, in much the same manner as a hardcopy photograph may be slid into a slotted picture frame. Such a casing could have a partially open face to allow access to the viewing screen of the flexible device. The casing might also be constructed of a clear plastic material to allow the user to see through the casing to the viewing screen of the device. Where a casing with a slot is used, the sound transmission tubing could be embedded in a predetermined location within the casing such that it opens over the flexible device's microphone when the flexible device is inserted into the slot.

Frequency Manipulation Software

A problem that arises when using a sound collector is that often many more frequencies of sounds are collected than the user actually wishes to hear. Furthermore, the frequencies that are of interest to the user may have less strength than others (and therefore may not be loud enough). In the context of the present invention, this problem can be conveniently solved by providing the handheld electronic device in question with a software program that is capable of eliminating unwanted sound frequencies and/or amplifying desired sound frequencies.

As an example, human heart sounds typically fall in a range less than about 150 hz. A test was performed recording a human heart sound using a stethoscope connected by a tube to an iPhone microphone. The recorded heart sounds turned out to be of sub-par quality. Then, commercially available audio frequency manipulation software applications were employed in conjunction with an embodiment of the invention similar to that shown in FIGS. 1A-1D. These software programs included the Thinklabs Stethoscope Application and an application entitled "My Baby's Beat" (an application intended to allow pregnant mothers to record their baby's heart sounds). By using this audio frequency manipulation software in conjunction with the invention, a much clearer sound output was achieved. Although many sound frequency augmentation, equalization and/or elimination software programs exist on the market and are known to those of skill in the art of digital sound manipulation, applicants are not aware of anyone proposing the use of such programs in conjunction with an acoustic collector mounted to a handheld electronic device, as proposed herein.

In a preferred embodiment, the present invention will be accompanied by a sound frequency manipulation software installed on the handheld electronic device and capable of amplifying certain frequencies and/or limiting or eliminating others. Because most users will not be familiar with the frequency range of the sounds they desire to listen to, it will be advantageous for the program to provide a simple visual frequency range selector tool so the user can actively vary which frequencies are augmented to identify the best possible sound output. Certain known frequency ranges for common applications may be indicated, e.g., approximately 20-150 Hz for human heart sounds, approximately 150-1200 Hz for most human lung sounds.

As just noted, the frequency manipulation software described above might function by amplifying certain sound frequencies relative to others, or by limiting or eliminating certain undesired sound frequencies. Any of the these techniques will be referred to herein in as "augmentation" or "augmenting" certain sound frequencies.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. An acoustic collection tool for a handheld electronic device comprising:
   a casing mountable to said handheld electronic device;
   a chestpiece attachable to said casing, said chestpiece having an aperture for carrying sound to a hole on the chestpiece;
   a hollow passage mounted to said casing for transmitting sound to a microphone, said hollow passage having a first opening and a second opening, and said hollow passage having an inner wall;
   wherein said hole of said chestpiece is configured to mate with either of said first opening and said second openings; and wherein mating said hole with said first opening will cause a distance through said hollow passage between said hole and said microphone to be longer than if said hole is mated to said second opening.

2. The acoustic collection tool of claim 1 wherein, when said hole is mated with one of said first and second openings, a projection at least partially obstructs a distal portion of said hollow passage.

3. The acoustic collection tool of claim 1 wherein said first and second openings lie on a curved hollow tube portion of said hollow passage, and wherein said hole lies near a perimeter of said chestpiece, and wherein said chestpiece may be rotated relative to said casing, and wherein a curvature of said curved hollow tube portion substantially matches an arc traced by said hole when said chestpiece is rotated relative to said casing.

4. The acoustic collection tool of claim 1 wherein, when said hole is mated to one of said first and second openings, a sealing structure simultaneously seals off the other of said first and second openings by forming a surface substantially flush with said inner wall while leaving an interior of said hollow passage substantially unobstructed.

5. The acoustic collection tool of claim 1 wherein said inner wall of said hollow passage is constructed of a first material along part of its length, and a second material along a different part of its length, and wherein said first material has different sound propagation properties than said second material.

6. The acoustic collection tool of claim 1 wherein at least a portion of said inner wall of said hollow passage is designed to resonate preferentially with a predetermined sound frequency.

7. The acoustic collection tool of claim 1 wherein at least a portion of said inner wall of said hollow passage is designed to dampen sound.

8. The acoustic collection tool of claim 1 wherein said chestpiece is equipped with electrocardiogram leads, and wherein said acoustic collection tool is designed to transmit electrocardiogram signals to said handheld electronic device.

9. An acoustic collection tool for a handheld electronic device comprising:

a casing mountable to said handheld electronic device;
a hollow passage mounted to said casing, said hollow passage having an inner wall;
a chestpiece attachable to said casing, said chestpiece having an aperture for carrying sound to said hollow passage; and
a microphone mounted within said hollow passage, said microphone capable of transmitting a signal to said handheld electronic device, wherein said microphone is mounted to a plug, and wherein said plug can be moved within said hollow passage to selectively change a position of said microphone within said hollow passage.

10. The acoustic collection tool of claim 9 wherein one or more sides of said plug that are inserted into said hollow passage are substantially flush with said inner wall when said plug is inserted into said hollow passage, such that varying the position of said plug within said hollow passage will effectively vary a size of said hollow passage.

11. The acoustic collection tool of claim 10 wherein said plug is made of compressible foam that must be compressed to pass through at least a portion of said hollow passage.

12. The acoustic collection tool of claim 9 wherein a width of said hollow passage varies along its length.

13. The acoustic collection tool of claim 9 wherein said inner wall of said hollow passage is constructed of a first material along part of its length, and a second material along a different part of its length, and wherein said first material has different sound propagation properties than said second material.

14. The acoustic collection tool of claim 9 wherein at least a portion of said inner wall of said hollow passage is designed to resonate preferentially with a predetermined sound frequency.

15. The acoustic collection tool of claim 9 wherein at least a portion of said inner wall of said hollow passage is designed to dampen sound.

16. The acoustic collection tool of claim 9 wherein said chestpiece is equipped with electrocardiogram leads, and wherein said tool is designed to transmit electrocardiogram signals to said handheld electronic device.

* * * * *